(12) United States Patent
DeBelser et al.

(10) Patent No.: US 9,192,712 B2
(45) Date of Patent: Nov. 24, 2015

(54) SECURITY FEATURES FOR A MEDICAL INFUSION PUMP

(75) Inventors: David DeBelser, Plymouth, MN (US); Michael L. Blomquist, Blaine, MN (US)

(73) Assignee: Smiths Medical ASD, Inc., Rockland, MA (US)

(*) Notice: Subject to any disclaimer, the term of this patent is extended or adjusted under 35 U.S.C. 154(b) by 899 days.

(21) Appl. No.: 12/416,584

(22) Filed: Apr. 1, 2009

(65) Prior Publication Data

US 2009/0270810 A1 Oct. 29, 2009

Related U.S. Application Data

(60) Provisional application No. 61/041,475, filed on Apr. 1, 2008.

(51) Int. Cl.
*A61M 5/168* (2006.01)
*A61M 5/142* (2006.01)
*G06F 19/00* (2011.01)

(52) U.S. Cl.
CPC ........... *A61M 5/142* (2013.01); *G06F 19/3468* (2013.01)

(58) Field of Classification Search
CPC .................... G06F 19/3468; A61M 5/142
USPC ........ 340/5.1, 5.2, 5.21, 5.22, 5.5, 5.51, 5.52, 340/5.53, 5.61, 5.82, 5.83, 5.85; 604/131, 604/67, 890.1, 891.1, 65–66; 600/554
See application file for complete search history.

(56) References Cited

U.S. PATENT DOCUMENTS

| | | |
|---|---|---|
| 2002/0015024 A1 | 2/2002 | Westerman et al. |
| 2002/0038392 A1* | 3/2002 | De La Huerga ................... 710/8 |
| 2002/0183693 A1 | 12/2002 | Peterson et al. |
| 2004/0039257 A1* | 2/2004 | Hickle ........................... 600/300 |
| 2004/0128162 A1 | 7/2004 | Schlotterbeck et al. |
| 2004/0193453 A1 | 9/2004 | Butterfield et al. |
| 2005/0055242 A1 | 3/2005 | Bello et al. |
| 2005/0086008 A1* | 4/2005 | DiGianfilippo et al. ......... 702/19 |
| 2005/0144043 A1 | 6/2005 | Holland et al. |
| 2005/0246416 A1 | 11/2005 | Blomquist |
| 2006/0047538 A1 | 3/2006 | Condurso et al. |
| 2006/0247606 A1 | 11/2006 | Batch |
| 2008/0033360 A1 | 2/2008 | Evans et al. |

(Continued)

FOREIGN PATENT DOCUMENTS

| | | |
|---|---|---|
| CN | 1759398 | 4/2006 |
| WO | WO03097123 | 11/2003 |
| WO | WO03097126 | 11/2003 |

OTHER PUBLICATIONS

Invitation to Pay Additional Fees with Partial International Search mailed Sep. 3, 2009.

(Continued)

*Primary Examiner* — Nabil Syed
(74) *Attorney, Agent, or Firm* — Patterson Thuente Pedersen, P.A.

(57) ABSTRACT

Various security features for a medical infusion pump are disclosed. The security features include providing dual verification for standing orders, allowing multiple levels of access rights to features of the medical infusion pump, and incorporating a security touch screen in the medical infusion pump. Methods of use and operation of these features are disclosed as well.

13 Claims, 14 Drawing Sheets

(56) References Cited

U.S. PATENT DOCUMENTS

| | | | |
|---|---|---|---|
| 2008/0033361 | A1 | 2/2008 | Evans et al. |
| 2008/0033402 | A1 | 2/2008 | Blomquist |
| 2008/0033749 | A1 | 2/2008 | Blomquist |
| 2008/0034323 | A1 | 2/2008 | Blomquist |
| 2008/0103531 | A1* | 5/2008 | Ginggen et al. ............ 607/2 |
| 2008/0126969 | A1 | 5/2008 | Blomquist |
| 2008/0306437 | A1 | 12/2008 | Jacobson et al. |
| 2009/0058598 | A1 | 3/2009 | Sanchez et al. |
| 2009/0165121 | A1 | 6/2009 | Kumar |
| 2013/0012876 | A1 | 1/2013 | DeBelser et al. |
| 2013/0012877 | A1 | 1/2013 | DeBelser et al. |

OTHER PUBLICATIONS

European Office Action for European Application No. 10189449.1 dated Jan. 23, 2014.
Second Chinese Office Action for Chinese Application No. 200980121204.8 dated Oct. 17, 2013.
Chinese Second Office Action for Chinese Application No. 201110092587.8 dated Mar. 4, 2013. English summary provided.
Chinese Notice of First Office Action for Chinese Application No. 200980121204.8 dated Dec. 18, 2013. English summary provided.
Chinese Notice of First Office Action for Chinese Application No. 201110092872.1 dated Oct. 9, 2012. English summary provided.
Australian Patent Examination Report No. 1 for Australian Application No. 2010236097 dated Nov. 13, 2013.
Chinese Notice of Second Office Action for Chinese Application No. 201110092872.1 dated Jul. 10, 2013. English summary provided.
Chinese Notice of First Office Action for Chinese Application No. 201110092887.8 dated Sep. 19, 2012. English summary provided.
European Search Report for European Application No. 10189449 dated Apr. 21, 2011.
European Search Report for European Application No. 10189447 dated May 4, 2011.
Application for File History for U.S. Appl. No. 13/619,575, filed Sep. 14, 2012, inventors DeBelser et al.
Application for File History for U.S. Appl. No. 13/619,481, filed Sep. 14, 2012, inventors DeBelser et al.
Chinese Office Action for Chinese Application No. 201110092887.8 dated Nov. 14, 2013. English summary provided.
Australian Patent Examination Report No. 1 for Australian Application No. 2010236098 dated Nov. 14, 2013.
Australian Patent Examination Report No. 2 for Australian Patent Application No. 2010236098 dated May 20, 2014.
European Office Action for European Application No. 10189447.5 dated Mar. 12, 2014.
Notice of Further Office Action for Chinese Application No. 200980121204.8 dated Jan. 26, 2015. English translation not available.
Australian Patent Examination Report No. 1 for Australian Application No. 2010236100 dated Feb. 10, 2014.
Final Rejection for Chinese Application No. 201110092872.1 dated Dec. 23, 2014. English translation not available.
Final Rejection for Chinese Application No. 201110092887.8 dated Nov. 25, 2014. English translation not available.
Notice of Preliminary Rejection for Korean Application No. 10-2010-7024610 dated May 29, 2015. English translation not available.
Notice of Preliminary Rejection for Korean Application No. 10-2010-7024819 dated May 29, 2015. English translation provided.
Notice of Preliminary Rejection for Korean Application No. 10-2010-7024820 dated May 29, 2015. English translation provided.
Canadian Office Action for Canadian Application No. 2,723,444 dated Jul. 7, 2015.

* cited by examiner

| User | User Class | Login Methods | Access Rights |
|---|---|---|---|
| John Doe | Physician | Password = pwd<br>Access # = 1234<br>Fingerprint = Doe.jpg | Administrator; Full |
| Josh Doe | Nurse | Password = nurse<br>Access # = 9876 | Program Access |
| Patient | Patient | Password = patient | Bolus; Request Assistance |
| Pharm Doe | Pharmacist | Password = drug<br>Fingerprint = pharm.jpg | Drug Access;<br>Administrator Rights |

1104 — User; 1108 — User Class; 1106 — Login Methods; 1110 — Access Rights; 1102; 1100

FIG. 11

| User Class | Members | Default Rights |
|---|---|---|
| Physician | John Doe<br>Jane Doe<br>Bob Doe | Administrator; Full Access |
| Nurse | Josh Doe<br>Nurse #2<br>Nurse #3 | Program Access |
| Patient | Generic Patient Login | Bolus; Request Assistance |
| Pharmacist | Pharm Doe | Drug Access; Administrator |

1208 — Members; 1206 — Default Rights; 1202; 1102; 1200

FIG. 12

SECURITY FEATURES FOR A MEDICAL INFUSION PUMP

CROSS-REFERENCE TO RELATED APPLICATIONS

The present application claims priority to U.S. Provisional Patent Application No. 61/041,475, filed Apr. 1, 2008, the disclosure of which is hereby incorporated by reference in its entirety.

TECHNICAL FIELD

The present disclosure relates to use of medical infusion pumps. In particular, the present disclosure relates to security and safety features used in conjunction with medical infusion pumps.

BACKGROUND

Patients at hospitals and other care centers regularly require controlled drug intake as a part of the patient's prescribed therapy. One form of controlled drug intake is accomplished by infusing fluidic drugs with a medical infusion pump.

Medical infusion pumps, in general, provide regulated drug delivery to a patient. These pumps are used to deliver a selected drug or other therapeutic agent to a patient at a predetermined rate that is programmed into the pump. A doctor, nurse, or other healthcare professional typically programs each medical infusion pump in accordance with a prescribed dosage of a drug or therapeutic agent. Once the medical infusion pump is programmed, it will execute that program regardless of any human errors introduced during the programming of the pump or creation of the pump protocol. Introduction of additional redundancies in verifying the programming of pumps can reduce errors in drug delivery to a patient.

Furthermore, medical infusion pumps can include a variety of functionality related to fluidic drug delivery. For example, medical infusion pumps can alter rates of drug delivery, can deliver boluses (additional drugs beyond the prescribed amount), and can accept reprogramming in accordance with different therapies, drugs, or patients. However, certain aspects of this functionality may be intended for use by a doctor, while other functionality may be intended for use by a nurse, and still further functionality may be intended for use by a patient. However, all of these settings and systems are generally available to all users of the medical infusion pump

SUMMARY

In a first aspect, a method of verifying a standing order in a medical infusion pump is disclosed. The method includes selecting a protocol for execution of a standing order in a medical infusion pump, and verifying the protocol in the medical infusion pump. The method also includes receiving confirmation of the protocol from a system external to the medical infusion pump, and, upon receiving confirmation of the protocol, allowing operation of the medical infusion pump in accordance with the protocol.

In a second aspect, a medical infusion pump is disclosed. The medical infusion pump includes a pump mechanism, a memory, and a programmable circuit arranged to control the pump mechanism and operatively connected to the memory. The programmable circuit is programmed to select a protocol for execution of a standing order in a medical infusion pump, and verify the protocol in the medical infusion pump. The programmable circuit is also programmed to receive confirmation of the protocol from a system external to the medical infusion pump, and upon receiving confirmation of the protocol, allow operation of the medical infusion pump in accordance with the protocol.

In a third aspect, an infusion pump network is disclosed. The infusion pump network includes a medical infusion pump and a computing system communicatively connected to the medical infusion pump. The infusion pump network is configured to execute program instructions to select a protocol for execution of a standing order in a medical infusion pump and verify the protocol in the medical infusion pump. The infusion pump network is also configured to execute program instructions to transmit confirmation of the protocol from the computing system to the medical infusion pump, and upon receiving confirmation of the protocol in the medical infusion pump, allow operation of the medical infusion pump in accordance with the protocol.

In a fourth aspect, a medical infusion pump is disclosed. The medical infusion pump includes a pump mechanism, a memory, and a programmable circuit arranged to control the pump mechanism and operatively connected to the memory. The programmable circuit is programmed to receive security data from a user and determine one or more access rights for the user based on the security data. The programmable circuit is also programmed to allow access to the medical infusion pump in accordance with the one or more access rights.

In a fifth aspect, a method of managing access to features in a medical infusion pump is disclosed. The method includes receiving security data from a user and determining one or more access rights for the user based on the security data. The method also includes allowing access to the medical infusion pump in accordance with the one or more access rights.

In a sixth aspect, a method of managing access to features in a medical infusion pump is disclosed. The method includes associating a user with a user class, the user class assigned one or more access rights in a medical infusion pump. The method further includes associating security data with the user, receiving the security data from the user, and determining the one or more access rights for the user based on the security data. The method also includes allowing access to one or more systems in the medical infusion pump in accordance with the one or more access rights.

In a seventh aspect, a medical infusion pump is disclosed. The medical infusion pump includes a pump mechanism, a memory, a display, and a programmable circuit arranged to control the pump mechanism and operatively connected to the memory and the display. The programmable circuit is programmed to receive a signal from the display, the signal corresponding to user interaction with the display of the medical infusion pump. The programmable circuit is also programmed to evaluate the signal and allow access to one or more settings incorporated into the medical infusion pump in response to evaluating the signal.

In an eighth aspect, a method of authenticating a user to use a medical infusion pump is disclosed. The method includes receiving a signal from a display of the medical infusion pump, the signal corresponding to user interaction with the display. The method also includes evaluating the signal and allowing access to one or more settings incorporated into the medical infusion pump in response to evaluating the signal.

In a ninth aspect, a medical infusion pump is disclosed. The medical infusion pump includes a pump mechanism, a memory, a touch screen display, and a programmable circuit arranged to control the pump mechanism and operatively connected to the memory and the display. The programmable circuit is programmed to associate a stored biometric signal with one or more user profiles stored in the medical infusion pump. The programmable circuit is also programmed to receive a biometric signal from the touch screen display, the biometric signal corresponding to user interaction with the display. The programmable circuit is further programmed to evaluate the received biometric signal based on the stored biometric signal, and upon evaluating the biometric signal, allow access to one or more settings incorporated into the medical infusion pump.

BRIEF DESCRIPTION OF THE DRAWINGS

FIG. 11 illustrates a user access record for managing user rights in a medical infusion pump, according to a possible embodiment of the present disclosure;

FIG. 12 illustrates a user class association record useable in a medical infusion pump, according to a possible embodiment of the present disclosure;

DETAILED DESCRIPTION

Figure 1:
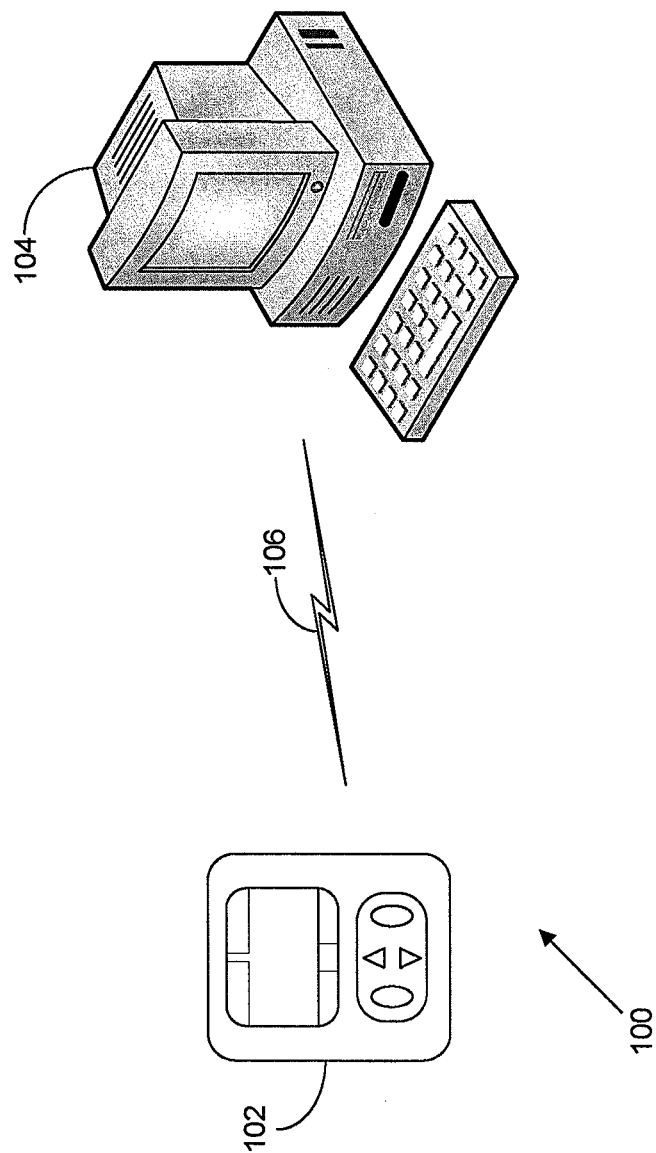
FIG. 1 illustrates a pump-computer communication system according to a possible embodiment of the present disclosure.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

The present disclosure relates generally to fluid delivery in a medical infusion pump, and management of pumps configured to deliver fluids to a patient. The present disclosure describes features of a medical infusion pump, as well as interactions that the medical infusion pump can have with users such as healthcare providers or others having physical or communicative access to the pump. Specifically, the present disclosure relates to safety and security features used in conjunction with a medical infusion pump to ensure that patients are treated with the correct drug or other therapeutic fluid, and receive the correct therapy using that drug/fluid. This can be accomplished, in general, by requiring multiple confirmations of each drug delivery, and by restricting access to certain settings or functionality in a medical infusion pump to those users (e.g. healthcare professionals) qualified to operate those aspects of the medical infusion pump.

The logical operations of the various embodiments of the present disclosure described herein are implemented as: (1) a sequence of computer implemented operations running on a computing system; and/or (2) interconnected machine modules within the computing system. Modules represent functions executed by program code such as commonly available programming languages or as the code found in a dynamic-link library (DLL). The implementation used is a matter of choice dependent on the performance requirements of the medical infusion pump and the computing systems with which it interfaces. Accordingly, the logical operations making up the embodiments of the present disclosure can be referred to alternatively as operations, modules, and the like.

I. Computing Environment Incorporating a Medical Infusion Pump

The following discussion is intended to provide a brief, general description of a suitable computing environment in which the invention may be implemented. Although not required, the invention will be described in the general context of computer-executable instructions being executed by a computer, for example, a hand held computer, a personal computing system, or a medical infusion pump.

FIG. 1 illustrates an exemplary embodiment of an infusion pump network 100 having a medical infusion pump 102, a computing system 104, and a communications link 106. The medical infusion pump 102 is configured to deliver therapeutic fluids, such as drugs, saline, or nutrition to a patient. Examples of medical infusion pumps 102 include ambulatory pumps, stationary pumps, and pole mounted pumps.

The computing system 104 is configured to execute computer-readable instructions, such as computer software. The computing system 104 can be located in a variety of locations such as the point of care (POC) where a patient is being treated, in a healthcare facility at a location remote from the POC, or even at an off-site location remote from the healthcare facility itself. In further embodiments, the medical infusion pump 102 acts as the computing system 104.

In the exemplary embodiment, the computing system 104 is programmed to generate and store pump protocols for execution in the context of a pump application program. Each pump protocol includes a series of pump parameters. Pump parameters refer to settings that define an operational aspect of a medical infusion pump. The pump parameters dictate the control of the pump.

By way of reference, pump protocols are collections of these pump parameters defining the variable operational characteristics of a medical infusion pump during application of a specific therapy, qualifier, and drug. The pump protocol includes a listing of operational parameters to be included in the pump, and correlates to an index for referring to a specific protocol containing a specific set of pump parameters. The index can be associated with a therapy, qualifier, and drug, and is either contained within the protocol or associated with a specific protocol. The pump protocol includes patient specific pump parameters and non-patient specific pump parameters. Patient specific pump parameters refer to those parameters which are set on a patient-by-patient basis, and for example include the basal delivery rate or bolus amount. Non-patient specific pump parameters refer to those parameters which are set for the pump to perform specific tasks, and do not account for the specific patient to which they are applied. These parameters are generally related to the pump, the infusion pump network, or the medical care to be provided by the pump and/or pump network. Non-patient specific pump parameters can include, for example, a range of permissible values for basal delivery, a range of values and patterns for basal delivery, a range of permissible values for boluses, a range of values and patterns for extended boluses, a starting value within a particular range of values, alarm values, protocols for data communication, and various flag settings. An example of a library of pump parameters accessible to a medical infusion pump is described below in conjunction with FIG. 7.

Also by way of reference, a pump application program is a program having instructions (e.g., executable code, rules, and/or data) that control operation of the pump for a specific therapy or type of delivery (e.g., continuous delivery, intermittent delivery, pain control, chemotherapy, total parenteral nutrition, etc.). For example, a pump application program might contain instructions that define operation of a pump to accomplish various of the pump parameters.

The communications link 106 connects the pump 102 and computing system 104. In various embodiments, the communications link 106 can include serial or parallel connections, wired or wireless connections, and a direct or networked connection to a computer. Additionally, the pump 102 and the computing system 104 can communicate using any protocol appropriate for data communication. Examples of network connections to a computer include Intranet, Internet, and LAN (e.g., Ethernet). Examples of wired connections to a computer include USB, RS-232, Firewire, and power-line modem connection. Examples of wireless connections include bluetooth, 802.11a/b/g, infrared (IR), and radio frequency (RF).

Further details regarding use of pump parameters and protocols in the context of an infusion pump network are discussed in U.S. patent applications Ser. Nos. 11/499,248, 11/499,240, 11/499,255, and 11/499,893, all filed Aug. 3, 2006, as well as U.S. patent applications Ser. Nos. 11/702,922 and 11/702,925 filed Feb. 5, 2007. Each of these patent applications is hereby incorporated by reference in its entirety.

Figure 2:
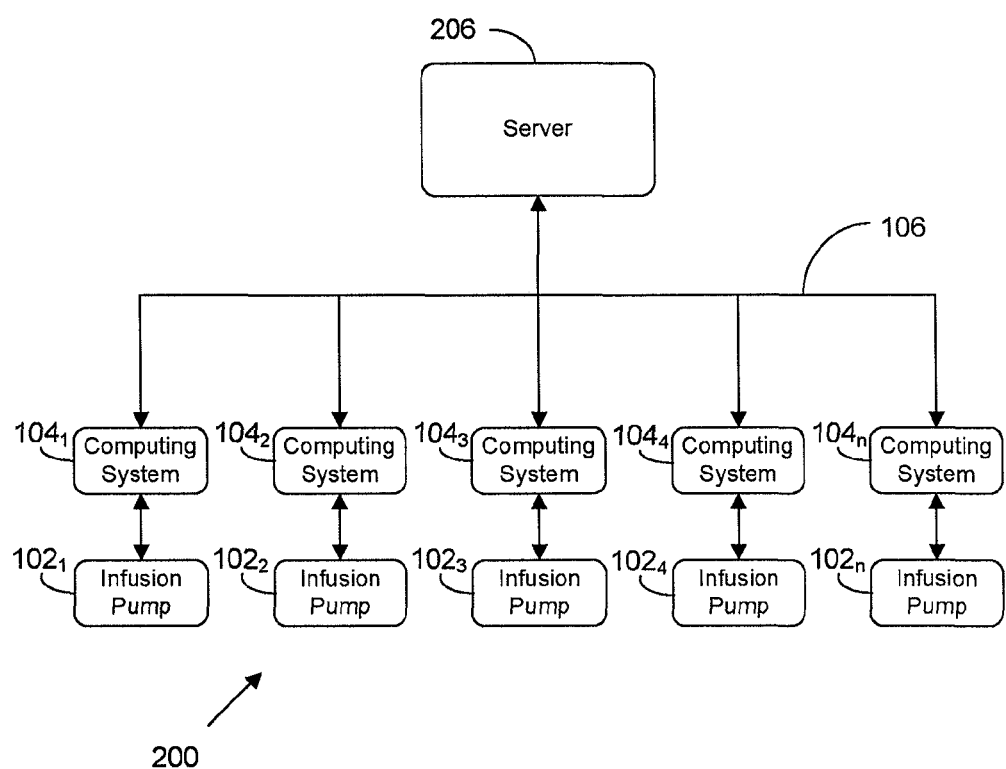
FIG. 2 illustrates an infusion pump network according to a possible embodiment of the present disclosure.

FIG. 2 illustrates an exemplary embodiment of an infusion pump network 200 having a server 206 networked with a plurality of computing systems $104_1$-$104_n$. The network 200 can be any wired or wireless network that enables data communication between the server, computing systems, and medical infusion pumps. Examples of networks include the Internet, Intranets, and LANs. Each computing system 104 can communicate with a medical infusion pump $102_1$-$102_n$ through a communication link 106.

In the exemplary embodiment, the individual computing systems $104_{1-n}$ execute software for generating and managing pump application programs and sets of pump operating parameters, and store information related to the associated medical infusion pump $102_{1-n}$. The pump application programs and sets of pump operating parameters can be stored on the server 206 and accessed by other individual computing systems $104_{1-n}$. The individual computing systems $104_{1-n}$ are also programmed to retrieve previously created pump application programs and sets of pump operating parameters that are stored on the server 206 for viewing, editing, and downloading to medical infusion pumps $102_{1-n}$. These pump application programs and pump operating parameters can be used to determine various fluid delivery algorithms, such as those described in greater detail herein.

The individual computing systems $1041$, are also programmed to communicate various information between the medical infusion pumps $102_{1-n}$ and the server 206. In certain embodiments, the individual computing systems $104_{1-n}$ are programmed to communicate pump events to the server for storage and later processing, such as cost and operational history data tracked in the medical infusion pumps $102_{1-n}$. In further embodiments, the individual computing systems $104_{1-n}$ are programmed to communicate messages generated in the pumps to external computing systems, including the server 206 and other devices, for notification of third-party caregivers of certain occurrences (e.g. exceptions or alarms) in the pump.

In alternative embodiments, the medical infusion pumps $102_{1-n}$ can directly communicate with the server to retrieve pump application programs and sets of pump operating parameters and to provide data relating to operation of the pump. For example, the medical infusion pumps $102_{1-n}$ can be loaded with client software such as a web browser and communicate directly with the network 200, either through a wired or wireless connection as described herein.

In other alternative embodiments, one or more of the computing systems (e.g. $104_{1-n}$) is not configured to communicate directly with one of the medical infusion pump $102_{1-n}$, but rather provides administrative access to the server 206 for generating, viewing, and editing pump application programs and sets of pump operating parameters, and for communicating data from the pump to the server. Additionally, servers, workstations, and other computing systems unaffiliated with the medical infusion pumps $102_{1-n}$ can be included in the network 200.

In yet other alternative embodiments, certain aspects of the software described herein execute in the server 206. For example, in certain embodiments the server functions as an application service provider that communicates user interface and other data entries in mark-up language such as HTML or some other language or protocol that allows a user to execute software from a remote location. In these embodiments, the server 206 can function as an application service provider in which the server provides access to the software for generating and storing pump application programs and pump protocols that a user can create and download to a medical infusion pump, as well as for managing user databases, pump histories, message and alarm distribution, and other events. For example, the server 206 could be located at a pump manufacture, pharmaceutical manufacture, pharmacist, or some other third party separate from the user. The server 206 in such an embodiment can be accessed either from an individual computing system 104 or by a medical infusion pump 102 that has networking capabilities and client software.

Example embodiments of a server 206 and a medical infusion pump 102 having a web browser are disclosed in U.S. patent application Ser. No. 11/066,425, which was filed on Feb. 22, 2005 and is entitled Server for Medical Device, the entire disclosure of which is hereby incorporated by reference.

Figure 3:
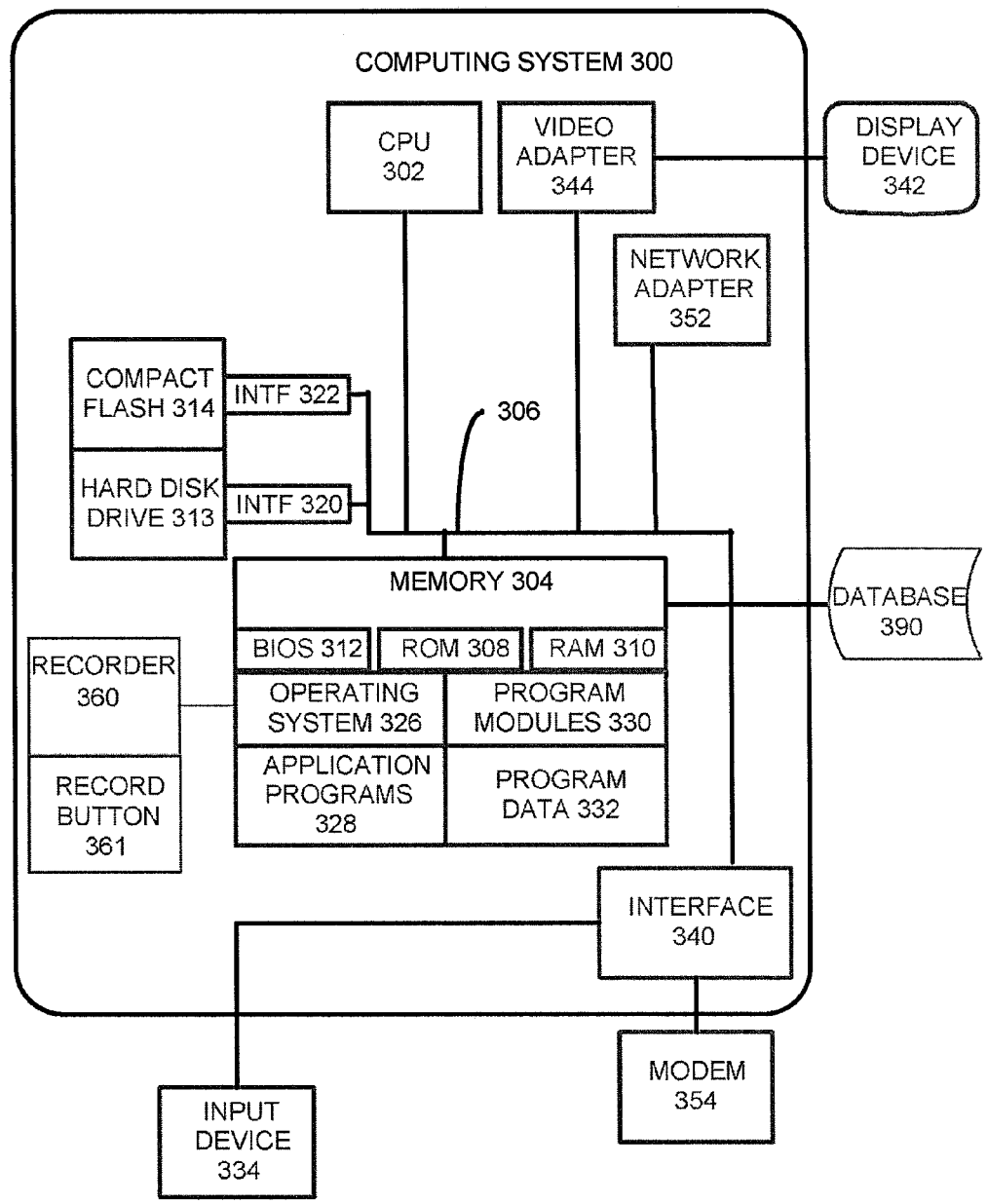
FIG. 3 illustrates the architecture of a computing system that can be used to implement aspects of the present disclosure.

FIG. 3 illustrates an exemplary architecture that can be used to implement aspects of the present disclosure, including the computing systems 104 or the server 206. The computing system architecture includes a general purpose computing device in the form of a computing system 300. The computing system 300 can be used, for example, as the computing system or server of FIG. 2, and can execute program modules included in the administrative software or user software disclosed below.

The computing system 300 includes at least one processing system 302. A variety of processing units are available from a variety of manufacturers, for example, Intel or Advanced Micro Devices. The computing system 300 also includes a system memory 304, and a system bus 306 that couples various system components including the system memory 304 to the processing unit 302. The system bus 306 may be any of a number of types of bus structures including a memory bus, or memory controller; a peripheral bus; and a local bus using any of a variety of bus architectures.

The system memory 304 can include read only memory (ROM) 308 and random access memory (RAM) 310. A basic input/output system 312 (BIOS), containing the basic routines that help transfer information between elements within the computing system 300, such as during start up, is typically stored in the ROM 308.

The computing system 300 can also include a secondary storage device 313, such as a hard disk drive, for reading from and writing to a hard disk (not shown), and/or a compact flash card 314.

The hard disk drive 313 and compact flash card 314 are connected to the system bus 306 by a hard disk drive interface 320 and a compact flash card interface 322, respectively. The drives and cards and their associated computer readable media provide nonvolatile storage of computer readable instructions, data structures, program modules and other data for the computing system 300.

Although the exemplary environment described herein employs a hard disk drive 313 and a compact flash card 314, other types of computer-readable media, capable of storing data, can be used in the exemplary system. Examples of these other types of computer-readable mediums include magnetic cassettes, flash memory cards, digital video disks, Bernoulli cartridges, CD ROMS, DVD ROMS, random access memories (RAMs), or read only memories (ROMs).

A number of program modules may be stored on the hard disk 313, compact flash card 314, ROM 308, or RAM 310, including an operating system 326, one or more application programs 328, other program modules 330, and program data 332. A user may enter commands and information into the computing system 300 through an input device 334. Examples of input devices might include a keyboard, mouse, microphone, joystick, game pad, satellite dish, scanner, digital camera, touch screen, and a telephone. These and other input devices are often connected to the processing unit 302 through an interface 340 that is coupled to the system bus 306. These input devices also might be connected by any number of interfaces, such as a parallel port, serial port, game port, or a universal serial bus (USB). Wireless communication between input devices and interfaces 340 is possible as well, and can include infrared, bluetooth, 802.11a/b/g, cellular, or other radio frequency communication systems. A display device 342, such as a monitor or touch screen LCD panel, is also connected to the system bus 306 via an interface, such as a video adapter 344. The display device 342 might be internal or external. In addition to the display device 342, computing systems, in general, typically include other peripheral devices (not shown), such as speakers, printers, and palm devices.

When used in a LAN networking environment, the computing system 300 is connected to the local network through a network interface or adapter 352. When used in a WAN networking environment, such as the Internet, the computing system 300 typically includes a modem 354 or other communications type, such as a direct connection, for establishing communications over the wide area network. The modem 354, which can be internal or external, is connected to the system bus 306 via the interface 340. In a networked environment, program modules depicted relative to the computing system 300, or portions thereof, may be stored in a remote memory storage device. It will be appreciated that the network connections shown are exemplary and other methods of establishing a communications link between the computing systems may be used.

The computing system 300 might also include a recorder 360 connected to the memory 304. The recorder 360 includes a microphone for receiving sound input and is in communication with the memory 304 for buffering and storing the sound input. The recorder 360 also can include a record button 361 for activating the microphone and communicating the sound input to the memory 304. The computing system can also include a database 390 for storage of data. The database 390 can be accessible via the memory 304 (either integrated therein or external to) and can be formed as any of a number of types of databases, such as a hierarchical or relational database.

A computing device, such as computing system 300, typically includes at least some form of computer-readable media. Computer readable media can be any available media that can be accessed by the computing system 300. By way of example, and not limitation, computer-readable media might comprise computer storage media and communication media.

Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium that can be used to store the desired information and that can be accessed by the computing system 300.

Communication media typically embodies computer-readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above should also be included within the scope of computer-readable media. Computer-readable media may also be referred to as computer program product.

Figure 4:
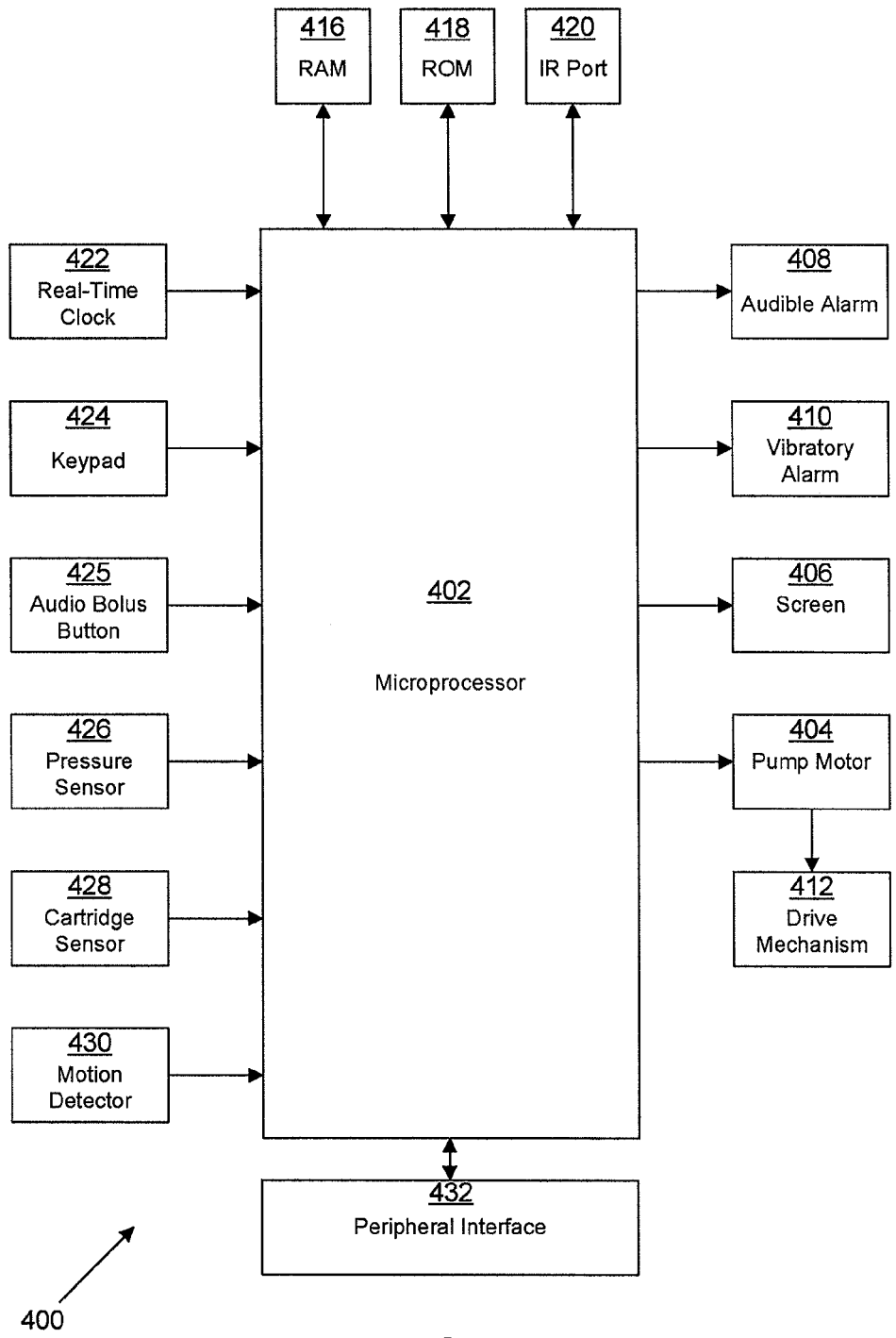
FIG. 4 illustrates the architecture of a pump that can be used to implement aspects of the present disclosure.

FIG. 4 illustrates the architecture of a medical infusion pump 400 that can be used to implement aspects of the present disclosure. In general, the medical infusion pump 400 is a programmable pump configured to deliver fluids (e.g. fluidic drugs) to patient, such as through use of an infusion set. The medical infusion pump 400 executes one or more application programs, as described above in conjunction with FIG. 1, to accomplish fluid delivery to a patient.

In the medical infusion pump 400, a microprocessor 402 is in electrical communication with and controls a pump motor 404, a screen 406, an audible alarm 408, and a vibratory alarm

410. Other embodiments can use a microcomputer, or any other type of programmable circuit, in place of the microprocessor.

The pump motor 404 drives a drive mechanism 412. The drive mechanism 412 delivers the therapeutic fluid to a patient. The drive mechanism can be connected to a plunger system, a peristaltic drive mechanism, or another type of fluid delivery system.

The screen 406 can have many different configurations such as an LCD screen. The screen 406 displays a user interface that presents various items of information useful to a patient or caregiver. In certain embodiments, the screen 406 is a touch screen display, such as a multi-touch display or other display accepting a signal based on pressure, heat, or other stimulus applied to the screen by a user. For example, the screen 406 can be a resistive touch screen panel, a surface acoustic wave panel, a capacitive touch screen panel, or any other types of touch-sensitive panels. In such embodiments, one or more buttons or other input regions can be displayed on the screen 406 to prompt input by a user, such as touching the screen with a finger, keycard, or other object. This input can be used for a variety of purposes, including to validate the identity of the user or to select/confirm options presented to the user. In certain embodiments, the screen 406 can include biometric capture capabilities, such as a fingerprint reader. One possible application of a display able to capture a signal from a user includes user authentication, and is discussed below in conjunction with FIGS. 13-15.

An alarm provides actual alarms, warnings, and reminders in the pump. The audible alarm 408 can be a beeper or otherwise provide audible notifications. Similar to other portable electronic devices such as a cellular telephone, the vibratory alarm 410 provides an alarm to either supplement the audio alarms or replace the audio alarm when an audible beep would be disruptive or not heard. A user can selectively enable or disable the audible 408 and vibratory 410 alarms. In one possible embodiment, however, both the audible 408 and vibratory 410 alarms cannot be disabled at the same time.

The microprocessor 402 is in electrical communication with a random access memory (RAM) 416 and a read only memory (ROM) 418, which are onboard the pump 400 but external to the microprocessor 402 itself. In one possible embodiment, the microprocessor 402 includes internal memory as well. The RAM 416 is a static RAM stores that data that can change over time such as pump settings and a historical log of events experienced by the medical infusion pump 400. The ROM 418 stores code for the operating system and the application programs. The ROM 418 can be any type of programmable ROM such as an EPROM.

An infrared (IR) port 420 is in electrical communication with the microprocessor. As explained in more detail below, the IR port 420 provides data communication with an external device such as a computer for programming an application program, programming pump settings, and downloading historical data logs. The medical infusion pump 400 can include other types of communication ports in place of or in addition to the IR port 420. Examples of other possible communication ports include a radio frequency (RF) port or a port that provides a hard-wired data communication link such as an RS-232 port, a USB port, or the like.

Optionally, an additional nonvolatile memory can be incorporated into the pump and interfaced with the microprocessor 402, such as a flash memory. This additional nonvolatile memory can be configured to store data collected by the pump, such as a history of events in the medical infusion pump, alarm and message information, user records for healthcare personnel authorized to operate the pump, and other information.

A real-time clock 422 provides a clock signal to the microprocessor 402. An advantage of having a real-time clock 422 is that it provides the program with the actual time in real-time so that the programs executed by the medical infusion pump can track and control the actual time of day that drug delivery and other events occur. Various durations described here are used for alerts, alarms, reminders, and other functions. In one possible embodiment, the timers are formed by the real-time clock 422 and software executed by the microprocessor 402.

A keypad 424 also provides input to the microprocessor 402. Although other possible types of keypads are possible, one type of keypad has four buttons and is a membrane-type of keypad, which provides resistance to water and other environmental conditions. The keypad 424 contains soft keys for which the function of the keys can change as a user executes different menu selections and commands.

An audio bolus button 425 optionally provides input to the microprocessor 402. The audio bolus button 425 can program the pump 400 to audibly administer a bolus of drugs or other therapeutic fluids without requiring visual confirmation using the pump. In an example embodiment, the audio bolus button 425 can be pressed a series of times to trigger bolus delivery of a selected volume, based on a preprogrammed trigger granularity. A single button press can represent a bolus of 5 grams, as selected by a user, and subsequent presses of the audio bolus button can represent multiples thereof.

Other inputs into the microprocessor 402 can include an occlusion sensor 426, which is sensitive to occlusions in the therapeutic fluid delivery line; a cartridge sensor 428, which is sensitive to the presence of a therapeutic fluid cartridge; and a motion detector 430, which detects motion of a gear (not shown) in the drive mechanism 412. In an exemplary embodiment, the cartridge sensor 428 includes one or more sensors configured to detect insertion of a therapeutic fluid cartridge. The pump 400 can detect the type of cartridge present via a mechanical interface, and can include in the pump software instructions regarding operation in conjunction with the cartridge. Examples of cassette sensing features are described, for example, in U.S. Pat. No. 5,531,697, filed on Apr. 15, 1994, issued on Jul. 2, 1996, and entitled "Systems and Methods for Cassette Identification for Drug Pumps."

A peripheral interface 432 allows additional systems to be added to the pump 400, such as various communication and functional systems. Example systems that can be interfaced with the pump include a bar code reader or a communication module, or other devices such as those devices described below in conjunction with FIG. 5.

Figure 5:
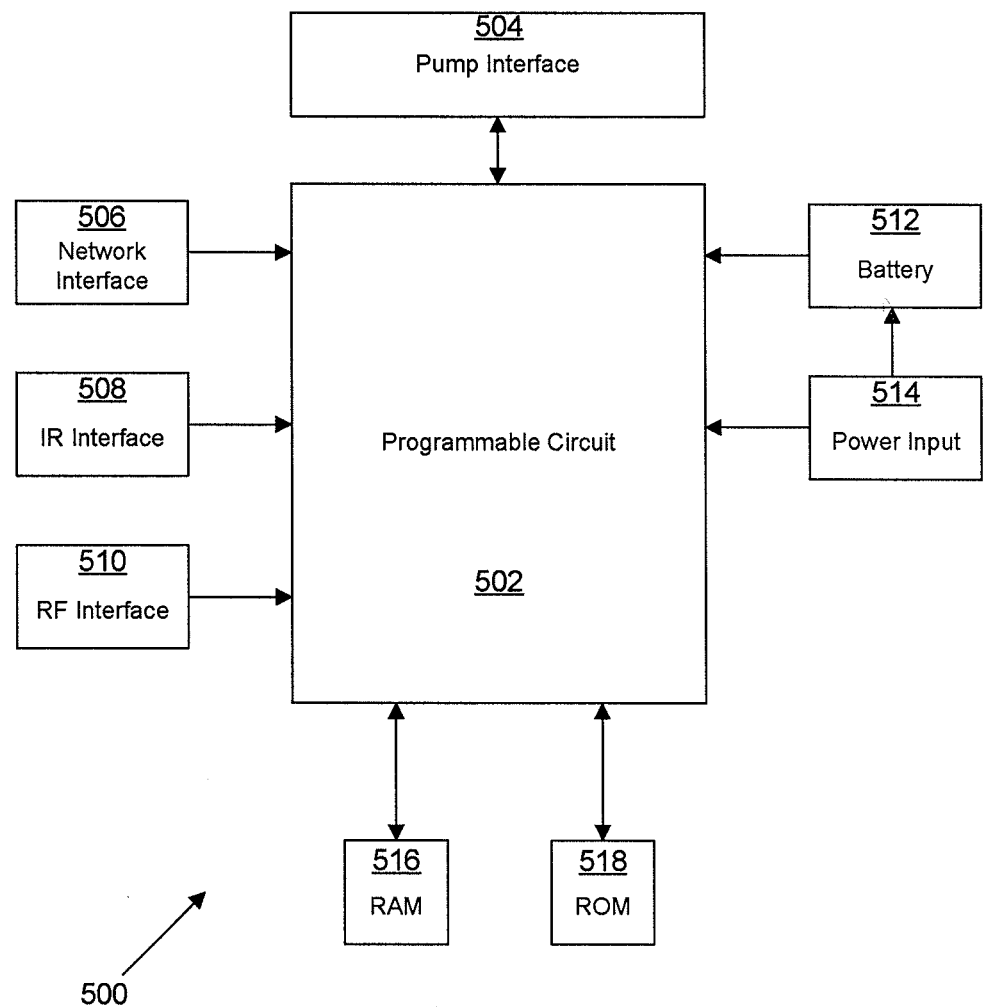
FIG. 5 illustrates the architecture of a pump peripheral device that can be used to implement aspects of the present disclosure.

FIG. 5 illustrates a peripheral device 500 that can interface with the medical infusion pump described in FIG. 4. The peripheral device 500 generally provides extended functionality to the medical infusion pump 400. In the embodiment shown, the peripheral device 500 provides extended communication and computation functionality to the medical infusion pump, thereby offloading a number of tasks from that system and freeing resources used for delivering fluids to the patient.

The peripheral device 500 includes a programmable circuit 502, which is configured to execute program instructions as directed by the microprocessor 402 of the medical infusion pump 400 and also as received from external computing systems. The programmable circuit 502 also optionally includes various additional operational logic configured to access memory, and to respond to the various interfaces to the programmable circuit. In one embodiment, the programmable circuit 502 includes a microcontroller. The microcontroller can be programmable in any of a number of programming languages, such as assembly language, C, or other low-level language. In alternate embodiments, the programmable circuit 502 includes a programmable logic device (PLD) such as a field programmable gate array (FPGA), Complex Programmable Logic Device (CPLD), or Power ASIC (Application Specific Integrated Circuit). In these embodiments, a hardware description language such as Verilog, ABEL, or VHDL defines operation of the programmable circuit.

The peripheral device 500 also includes an electrical interface 504 communicatively interfaced with the programmable circuit. The electrical interface 504 provides an electrical and data connection between the programmable circuit 502 and connecting circuitry of a medical infusion pump (e.g. the peripheral interface 432 of the medical infusion pump of FIG. 4). In the embodiment shown, the electrical interface 502 can be a serial or parallel interface, such as a USB interface, which allows the peripheral device to both (1) transmit and receive data along the interface, and (2) receive/transmit electrical power, such as to power either the medical infusion pump 400 or peripheral device 500.

A variety of additional interfaces also connect to the programmable circuit 502, including a network interface 506, an infrared interface 508, and a wireless interface 510. Each of these interfaces provides data communications connections with corresponding computing systems external to the medical infusion pump. The network interface 506 provides a wired connection to a packet-based, IP-addressable network, such as the Internet or a Local Area Network. The infrared interface 508 provides a direct device-to-device connection allowing data communication with nearby handheld or portable devices, and allowing the peripheral device 500 to receive data from such devices. The wireless interface 510 also provides a data connection to external computing systems, and can use any of a number of wireless communication protocols or networks, such as 802.11a/b/g/n, mesh networking, or some proprietary RF communication protocol. Other interfaces can be integrated into the peripheral device 500 or the medical infusion pump 400 as well, depending upon the particular implementation and desired communication systems used with the medical infusion pump.

The peripheral device 500 also includes a battery 512 and power input 514 interfaced to the programmable circuit 502. The battery 512 provides a power source to the circuitry in the peripheral device 500, and can also provide power to the medical infusion pump 400 via the pump interface 504. In certain embodiments, the battery is a rechargeable Lithium-ion battery pack that is rechargeable via the power input 514. The power input 514 receives power from an external source (e.g. an external AC plug), and converts that for use in the peripheral device (as distributed by the programmable circuit 502) and for recharging the battery 512.

The peripheral device also includes various types of memory communicatively interfaced to the programmable circuit, including a RAM 516 and a ROM 518. The RAM 516 and ROM 518 are used to execute program instructions provided to the peripheral device, such as for managing data input/output for the medical infusion pump. Additional memory types, such as a flash memory, can be used as well.

In certain embodiments, the peripheral device 500 can be incorporated into the medical infusion pump 400 of FIG. 4. In such embodiments, the programmable circuit 502 can be eliminated, with the various units interfaced thereto directly connecting to the microprocessor 402 of that system. In other embodiments, the peripheral device is separate from the medical infusion pump, requiring interface circuitry 504 and 432 for forming a connection therebetween.

Additional functionality can be included in the peripheral device 500 as well, based on the specific functionality desired for use with the medical infusion pump. Example additional functionality can include input/output devices, such as a bar code reader, fingerprint scanner, or other biometric reader.

Figure 6:
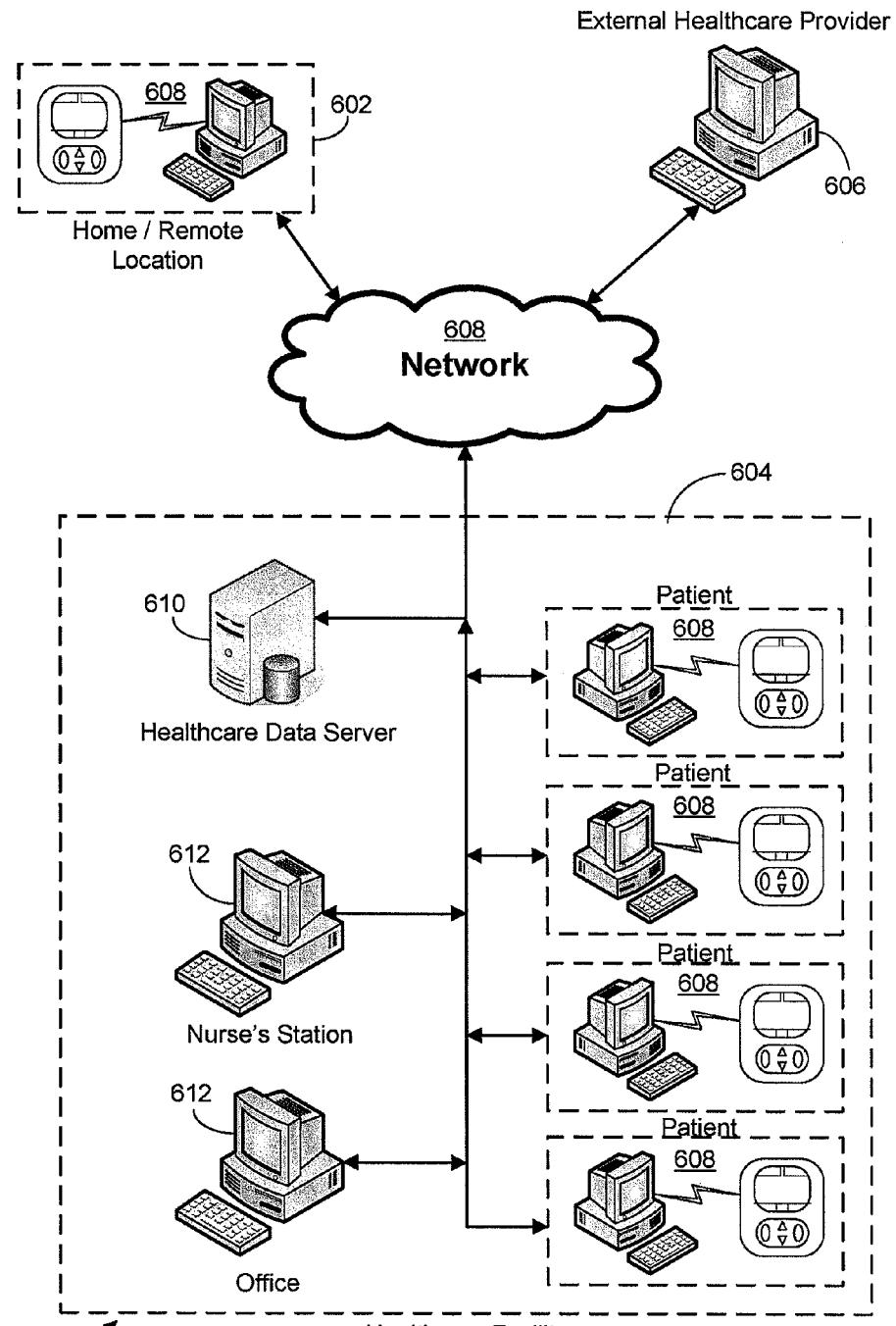
FIG. 6 illustrates a possible layout of a medical care network incorporating medical infusion pumps, according to a possible embodiment of the present disclosure.

Referring now to FIG. 6, a possible layout of a medical care network 600 is shown in which medical infusion pumps and infusion pump networks are used, according to a possible embodiment of the present disclosure. The medical care network 600 relates patients and healthcare professionals to each other using a variety of computing systems and medical devices, such as servers, medical infusion pumps, and other computing systems. As such, the medical care network illustrates one possible example of the network 100 illustrated in FIG. 1.

In the embodiment shown, the medical care network includes one or more medical infusion pumps, one or more computing systems that can be communicatively connected to those medical infusion pumps, one or more servers managing data relating to the medical infusion pumps, and other computing systems used by patients or healthcare professionals (e.g. nurses, doctors, pharmacists, or other clinicians). Details regarding the specific network 600 shown are described below; however, the network 600 is intended as exemplary, and various additional systems and devices can be included which are not currently shown.

In the embodiment shown, the medical care network 600 includes and interconnects a number of different physical entities/locations, including a home or remote location 602, a healthcare facility 604, and an external healthcare provider 606. The home or remote location 602 corresponds to a location outside of a healthcare facility at which a user may want to use a medical infusion pump, and may need to communicate data with a healthcare professional or with a server, such as for monitoring the status of the medical infusion pump. Each location can include, for example, an infusion pump network 608, such as the network described above in conjunction with FIG. 1.

The healthcare facility 604 corresponds generally to a hospital or clinic at which a number of patients may reside, as well as entities related to the facility (e.g. affiliated clinics or other institutions). In the embodiment shown, the healthcare facility 604 is arranged to accommodate a number of patients, by providing those patients with a medical infusion pump and a computing system for data communications with the pump. In the embodiment shown, the various patients can each be associated with an infusion pump network 608 such as shown in FIG. 1. The infusion pump networks 608 within the healthcare facility 604 can correspond to networks present in patient rooms, or computing networks surrounding a patient at the facility. Other possibilities for the configuration of the infusion pump networks 608 can exist as well.

The healthcare facility 604 further includes a healthcare data server 610 and a plurality of computing systems 612 not directly associated with the medical infusion pumps or infusion pump networks 608. The healthcare data server 610 and computing systems 612 are typically used by healthcare professionals for patient monitoring and care management, billing, and other purposes.

Each of the computing systems at the healthcare facility 604, including those interfaced with medical infusion pumps, are communicatively interconnected, allowing communication among the various infusion pump networks 608 and with the healthcare data server 610 and computing systems 612. The systems can be communicatively connected by any of a variety of communicative connections, including various wired and wireless Local Area Network connections.

The external healthcare provider 606 can correspond to various remote healthcare providers or healthcare-related entities, such as remote physicians, remote specialists, health insurance companies, or other entities. The external healthcare provider 606 generally receives a certain subset of the data related to one or more patients within the network 600, such as test information, billing information, diagnosis information, or other information.

Each of the entities within the network 600 are communicatively interconnected by a network 614, which represents a communication network in which data can be transferred, such as the Internet or some other Wide Area Network (LAN or WAN). The network 614 interconnects the various locations and computing systems at those locations, allowing data communication among the various locations. Through use of the network 614, remote locations can store or access information from other locations and/or systems. For example, the external healthcare provider 606 can access information stored on the healthcare data server 610 at the healthcare facility 604. Or, data can be uploaded to the healthcare facility from one of the local (at the facility) infusion pump networks 608, or remote infusion pump networks 608 at one of the remote locations 602. Other examples of data sharing and data communications are possible as well.

Figure 7:
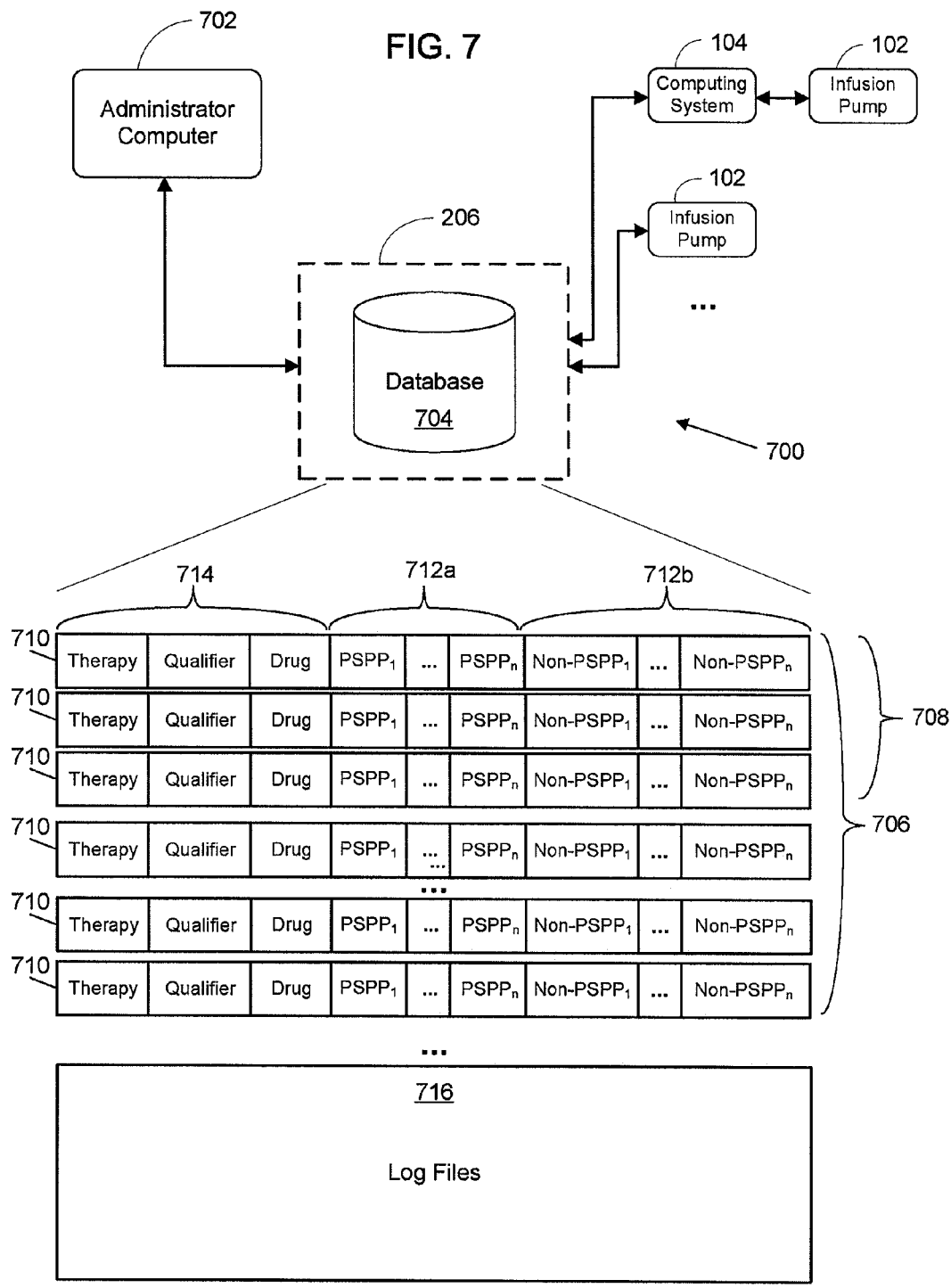
FIG. 7 is a further example infusion pump network according to a possible embodiment of the present disclosure.

FIG. 7 illustrates a schematic architecture of a medical infusion pump network 700 according to an exemplary embodiment. In certain embodiments, the medical infusion pump network 700 can be implemented within the medical care network 600 of FIG. 6, using components discussed above in FIG. 2. The various aspects of the medical infusion pump network 700 can be located at a healthcare facility, a remote facility, or at a patient's location (within or remote from the healthcare facility).

The medical infusion pump network 700 includes an administrator computer 702 communicatively connected to the server 206 of FIG. 2, which includes a database 704. The medical infusion pump network 700 also includes one or more medical infusion pumps 102 and computing systems 104.

The administrator computer 702 and computing systems 104 are systems such as those described above in conjunction with FIG. 3. The administrator computer 702 includes administrative software installed on or accessible to the computer for generating one or more libraries 708 of pump protocols 710 for use in the medical infusion pumps 102.

In the present disclosure, libraries refer to collections of pump protocols generated using the administrative software described herein. Libraries can be stored in files, databases, or other data structures. Libraries contain pump protocols as well as indices pointing to the protocols, and are loaded in user software to select a specific pump protocol for operation of a medical infusion pump.

The computing systems 104 include user software for accessing one or more libraries 708 of protocols 710 and programming a medical infusion pump 102 with a protocol 710 or a library 708. In one possible embodiment, the computing systems 104 are optional in that the user software resides directly on the medical infusion pumps 102. An exemplary embodiment of the user software is described below in FIGS. 26-41.

The medical infusion pumps 102 connect either to a computing system 104 or directly to the server 206, and are described above in conjunction with FIGS. 4-5. In a first embodiment, the medical infusion pumps 102 are configured to accept a pump protocol from the server 206 or the computing system 104. In a second embodiment, the medical infusion pumps 102 are configured to accept a library 708 of pump protocols 710 directly from the server 206 or from the computing system 104.

The database 704 contains pump protocol data 706 and log files 716. The pump protocol data 706 forms a plurality of libraries 708 which in turn each include a number of protocols 710. Each protocol 710 is stored as a data record, and includes a set of parameters, including patient specific pump parameters $712a$ and non-patient specific pump parameters $712b$, as described above. Each library 708 can contain one or more pump protocols 710.

The log files 716 include log data regarding access and usage of the libraries 708, and can include information related to the administrator computer 702, the medical infusion pumps 102, or the computing systems 104 authorized to connect to the server 206. In one possible embodiment, the log files include access records, which record instances in which medical infusion pumps 102 access a library 708 on the server 206.

B. Programmable Features Incorporated into a Medical Infusion Pump Network

FIGS. 1-7, above, describe certain aspects of medical infusion pumps and networks including medical infusion pumps, including various types of computing systems and communicative connections used in management and operation of the pumps. Now referring to FIGS. 8-15, applications of specific features incorporated into a medical infusion pump or a network including a medical infusion pump are described.

The applications and features described herein can be implemented, at least in part, in software, programmable hardware, and user interfaces integrated into the medical infusion pump, or a computing system interfaced with one or more medical infusion pumps. For example, one or more features are implemented in a pump application program able to be loaded onto and execute on a medical infusion pump. These programmable features relate to confirmation of pump protocols and user authentication for accessing features in the medical infusion pump.

1. Dual Verification of Standing Orders in a Medical Infusion Pump

Figure 8:
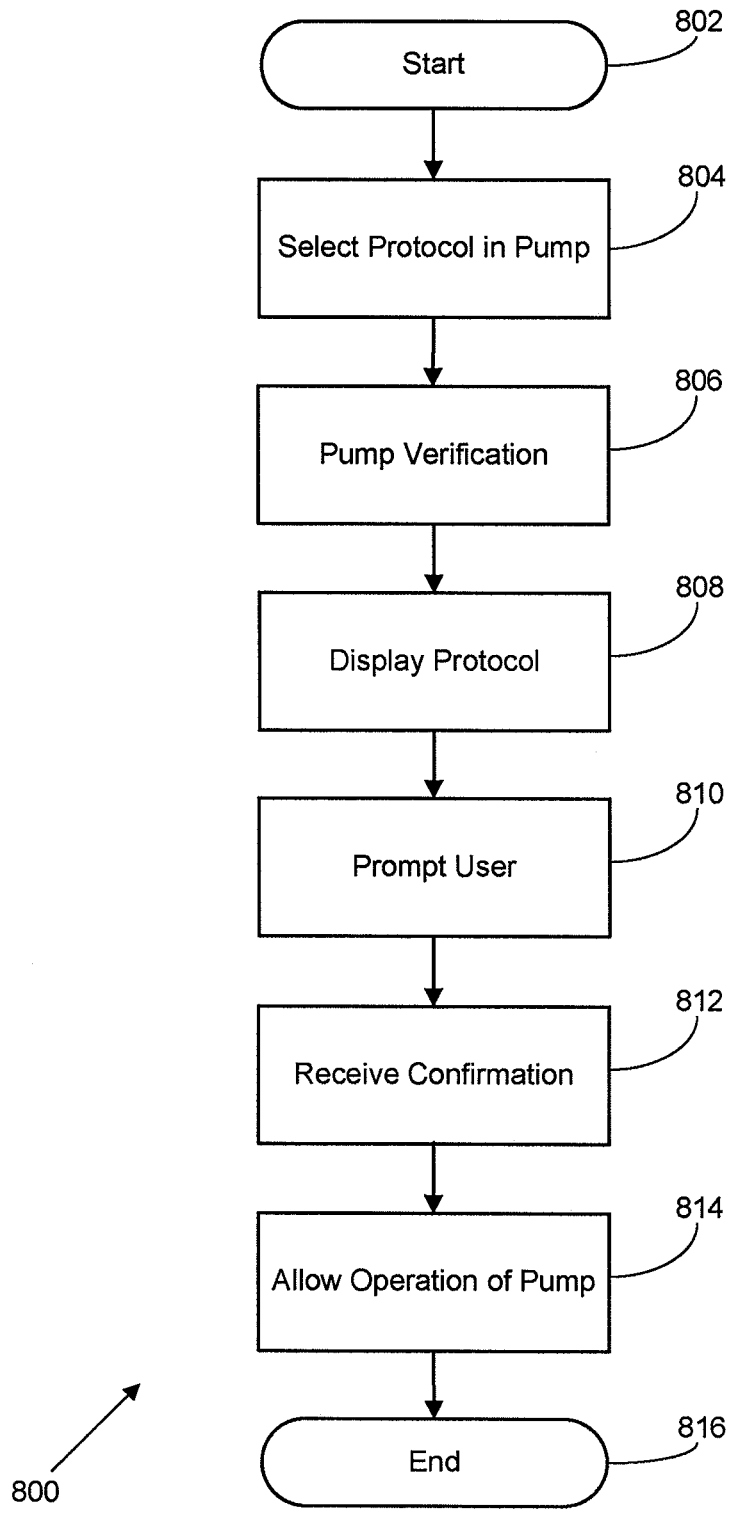
FIG. 8 illustrates a flowchart of methods and systems for verifying a standing order in a medical infusion pump, according to a possible embodiment of the present disclosure.
Figure 9:
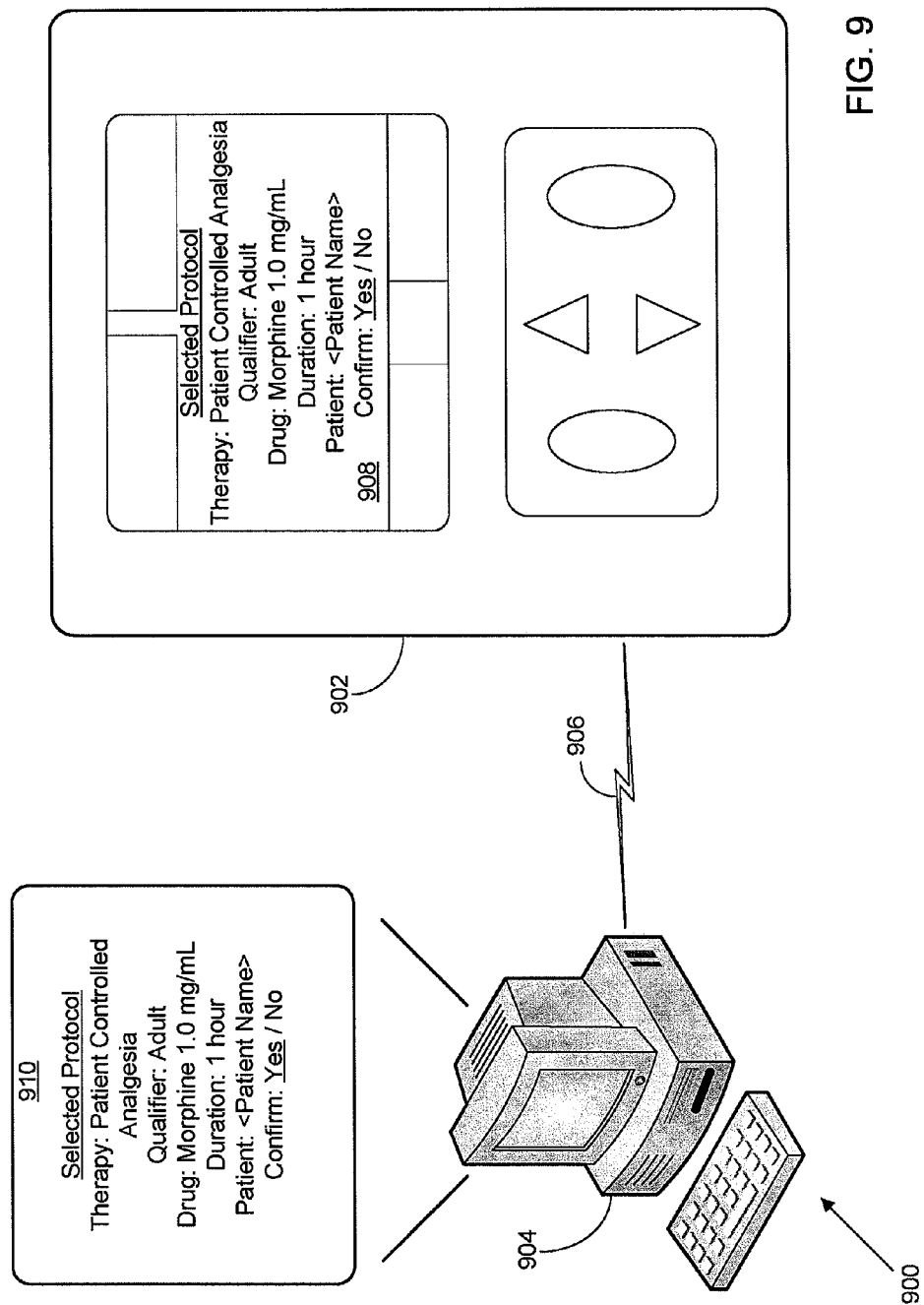
FIG. 9 is a schematic view of an infusion pump network configured for dual confirmation of a standing order, according to a possible embodiment of the present disclosure.

Now referring to FIGS. 8-9, systems and methods for verifying a standing order in a medical infusion pump are described. Generally, caregivers administer only those medications for which the physician has written and signed an order. The physician's order directs caregivers to provide care to a patient in accordance with the generalized instructions provided. Nurses and other caregivers providing drugs or other therapies to a patient are expected to do so accurately. The accuracy standard is expressed as "five rights" for patient care; that is, that the right patient receives the right drug, at the right dose, by the right route, and at the right time.

The systems and methods described are intended to improve safety in delivering fluids to a user using a medical infusion pump. Fluid delivery in a pump is likewise intended to be error-free, and consistent with a standing order. A standing order in a medical infusion pump corresponds to the generally prescribed use of a medical infusion pump to delivery fluids to a user at a specified rate and in accordance with a proper therapy, qualifier and drug (as explained above in FIGS. 1 and 7). By following the standing order associated with a patient, the medical infusion pump is ensured to deliver drugs and other fluids according to the correct pump protocols and to the right patient.

FIG. 8 illustrates a flowchart of a process 800 for verifying a standing order in a medical infusion pump, according to a possible embodiment of the present disclosure. The process provides additional verification of a standing order, as reflected in a programmed pump protocol, and identified by the therapy, qualifier, drug, and other patient information relevant to fluid delivery, to improve error rates and improve the "five rights" accuracy of the medical infusion pump. For example, the medical infusion pump can require a check of the accuracy of the pump protocol (e.g. by comparing the pump protocol to the sensed cartridge inserted in the pump), and can request independent verification of the protocol (e.g. the standing order) from an external computing system.

The process 800 is instantiated at a start operation 802, which corresponds to initializing a medical infusion pump for operation. The start operation 802 includes, for example, associating the medical infusion pump with a patient and powering on the pump. In certain embodiments, the start operation 802 includes communicatively connecting the medical infusion pump with computing systems in an infusion pump network.

A protocol selection module 804 selects a protocol for use in a medical infusion pump. The protocol selection module 804 selects the protocol from among a number of protocols, such as could be found in a library of protocols, as described in conjunction with FIG. 7, above. The protocol selection module 804 can execute on either the medical infusion pump or a computing system communicatively connected to the medical infusion pump in an infusion pump network, such as the network 100 of FIG. 1 or the network 600 of FIG. 6.

In some embodiments, the protocol selection module 804 prompts a user (e.g. a nurse, a physician or other clinician) to select a protocol for use in conjunction with a prescribed therapy, or a qualifier for that therapy, or a drug to be delivered to a patient, or all three of these aspects. In other embodiments, the protocol selection module 804 identifies possible protocols for use in conjunction with a drug or therapy, and prompts a user for selection from among a group of possible protocols useable in the medical infusion pump.

The protocol selection module 804 results in selection of a protocol useable by the medical infusion pump to accomplish execution of the standing order in accordance with physician direction. However, additional verification of the protocol is required to ensure that a correct protocol has been selected.

A pump verification module 806 verifies that the selected protocol is appropriate based on information available at the pump. The pump verification module 806 verifies a standing order (e.g. a particular use of a pump protocol selected via the protocol selection module 804) by displaying for review various aspects of the pump protocol and other information. For example, the pump verification module 806 allows a user to view and verify various aspects of a pump protocol, including the various parameters encompassed by the pump protocol and the therapy, qualifier, and/or drug used to select the protocol. Examples of the parameters that are verifiable by a user include a range of permissible basal delivery rates, a bolus amount, a fluid delivery amount, a range of values and patterns for extended boluses, alarm values, or protocols for data communication. Other information can be displayed for verification as well.

The pump verification module 806 also optionally requires verification that the patient with which the pump is associated is properly associated with the standing order (e.g. a child patient is not being administered an adult dosage, or vice versa), and that the cartridge installed into the medical infusion pump corresponds to the drug and fluid delivery parameters in the pump protocol. Other verification procedures can be performed as well.

The pump verification module 806 preferably requires a user, such as a healthcare professional, to verify the protocol on the pump in accordance with the standing order. The verification can be performed by visual inspection of the pump parameters, drugs used, and other aspects of the standing order displayed on the medical infusion pump, as is shown in the example display of FIG. 9. In an alternative embodiment, one or more of the parameters incorporated into the pump protocol can be verified by the medical infusion pump (e.g. the drug, by comparing the protocol to the cartridge inserted into the pump).

A display module 808 displays the protocol to a healthcare professional, such as the nurse, doctor, or other clinician, on a computing system separate from the medical infusion pump. The display module 808 displays a variety of information relevant to the protocol, including various parameters and other information about the patient and manner of delivery. As described in conjunction with the pump verification module 806, this information can optionally include the patient's name, as well as a therapy, a qualifier, and a drug to be delivered by the medical infusion pump, as well as parameters for use of that therapy qualifier and drug. These pump parameters can include, in various embodiments, a delivery rate, allowed adjustments to the delivery rate (e.g. hard and soft limits on the rate), allowed refills of the fluid cartridge associated with the pump, the name of the ordering doctor, and other information that is typically included within a standing order for use of a protocol. In certain embodiments, the display module 808 displays analogous information to that displayed on the medical infusion pump by the verification module 806.

In a possible embodiment, the display module 808 causes the protocol information to be displayed on a display of a computing system communicatively connected to the medical infusion pump, such as a local computing system that is part of an infusion pump network (e.g. the infusion pump network of FIG. 1). In other embodiments, the display module 808 causes the protocol information to be displayed on a display of a computing system remotely located from the medical infusion pump, and requires independent confirmation of at least one aspect of the protocol by another clinician, nurse, doctor, or other healthcare provider (separate from the healthcare provider initializing the pump locally).

Generally, the computing system displaying the protocol and other information related to programming the medical infusion pump receives a copy of the protocol from the medical infusion pump, and displays the same information as is displayed on the medical infusion pump. However, in certain embodiments, more or less information can be displayed, with sufficient consistency such that the caregiver viewing the protocol on the computing system can determine that the same protocol is referenced on both the computing system and the medical infusion pump. For example, various pump parameters in a named pump protocol could be displayed on the medical infusion pump, but only the name (and possibly a subset of those pump parameters) might be displayed on the computing system. Other arrangements are possible as well.

A prompt module 810 requests that a healthcare provider confirm the displayed elements of the protocol on the external computing system to again verify that the patient's "five rights" are followed in accordance with the standing order. The prompt module 810 requires an analogous confirmation from a healthcare provider that the protocol programmed into the medical infusion pump is appropriate based on the planned treatment of that patient (e.g. based on the standing order). A confirmation receipt module 812 corresponds to the medical infusion pump receiving confirmation of the protocol from the external computing system. In one embodiment, the confirmation received from the external computing system is a confirmation message indicating that the protocol is correct; in other embodiments, additional messages, amendments to the protocol, and other operations may be included in the communication to the medical infusion pump.

An operation module 814 allows the medical infusion pump to commence operation using the protocol, in accordance with the standing order. In the process 800, although various of the modules can be executed in different orders, the operation module 814 is reached only after the confirmation receipt module 812 and the pump verification module 806. So, two independent confirmations are required of the protocol by a nurse or other caregiver prior to allowing operation of the medical infusion pump. Requiring separate, independent confirmation of pump parameters on the medical infusion pump and on separate computing systems and pumps reduces the likelihood of errors occurring in programming the medical infusion pump, thereby improving patient care. Operational flow in the process terminates at an end operation 816, which corresponds to completion of the process 800 and allowance of the medical infusion pump to initiate or continue operation in accordance with the verified protocol (i.e. in accordance with the standing order).

FIG. 9 is a schematic view of an infusion pump network 900 configured for dual confirmation of a standing order, according to a possible embodiment of the present disclosure. The infusion pump network 900 generally corresponds to the infusion pump network 100 of FIG. 1, but illustrates an embodiment in which confirmation of pump protocols are required prior to operation of a medical infusion pump in accordance with the pump protocol (and associated standing order).

The infusion pump network 900 includes a medical infusion pump 902 communicatively connected to a computing system 904 via a communication link 906. The medical infusion pump 902 can be any of a variety of medical infusion pumps, such as the one described in conjunction with FIGS. 4-5. Likewise, the computing system can be any of a number of general or specific use computing systems, such as the system described in FIG. 3. The communication link 906 can be any of the communication link types described in FIG. 1.

As illustrated, the medical infusion pump 902 includes a display 908 and a keypad 909, and the computing system 904 also includes a display 910 and keyboard 911. This allows each of these systems to (1) display a pump protocol selected for use in the medical infusion pump and (2) receive confirmation inputs from a user which indicate that the protocol is/is not correct in view of the standing order.

As shown in FIG. 9, information relating to the protocol is displayed on a display 908 of the pump 902 and a display 910 of the computing system 904. The information, as shown, includes a name of the therapy, qualifier, and drug used in selecting the protocol, as well as a duration of operation of the protocol, the name of the patient, and a confirmation prompt. Additional information can be displayed on one or both of the displays, such as information about the pump parameters included in the pump protocol. As previously mentioned, these pump parameters include, for example, a range of permissible basal delivery rates, a bolus amount, a fluid delivery amount, a range of values and patterns for extended boluses, alarm values, or protocols for data communication.

2. Security for Select Features

Figure 10:
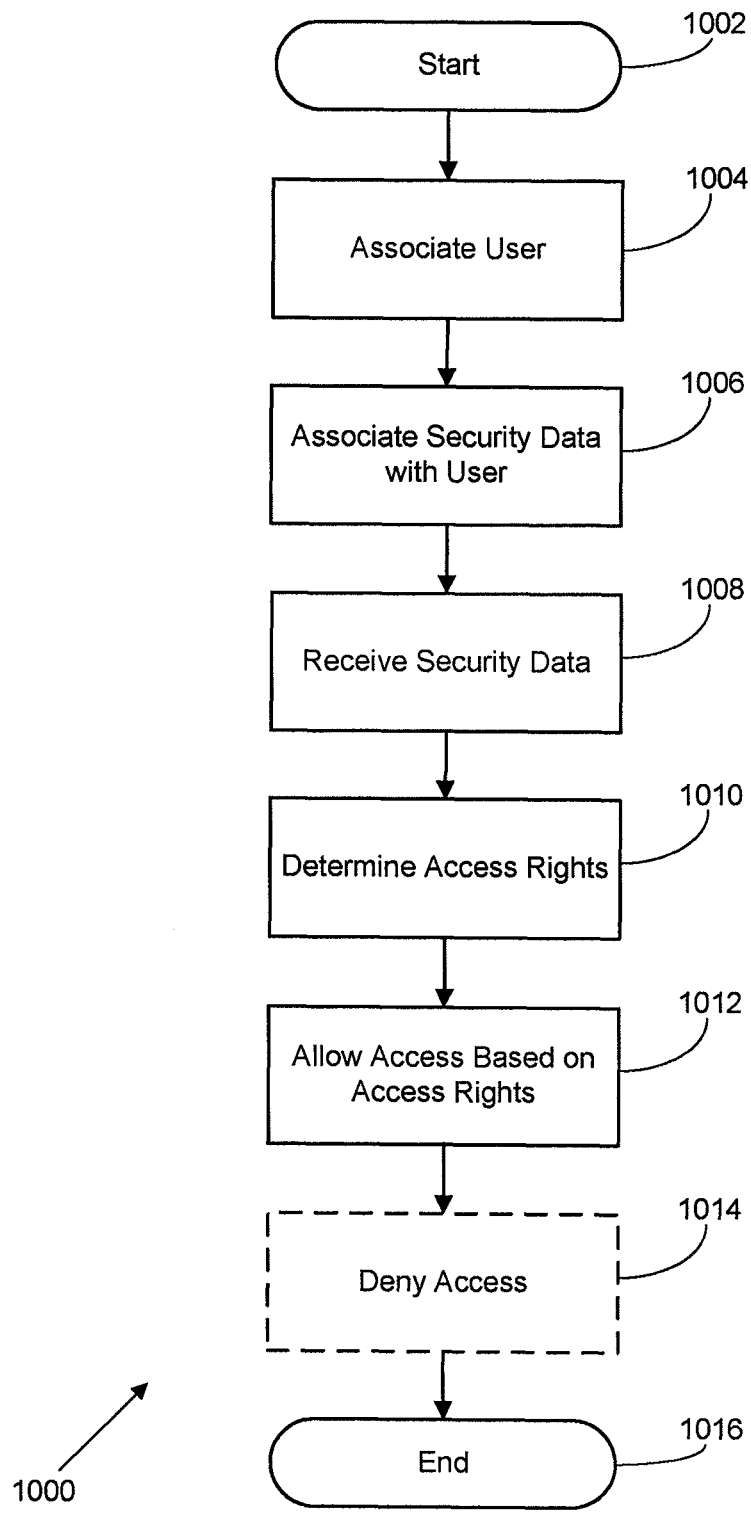
FIG. 10 illustrates a flowchart of methods and systems for managing access to features in a medical infusion pump, according to a possible embodiment of the present disclosure.

Referring now to FIGS. 10-12, systems and methods are disclosed for managing access to various features that can be included in a medical infusion pump. The systems and methods disclosed in these figures operate in conjunction with a medical infusion pump such as is disclosed in FIG. 4-5, as well as any peripheral equipment providing extended functionality to the pump (e.g. a bar code scanner or other peripheral device). By managing access to the various hardware and software features and settings of the medical infusion pump, the pump provides enhanced safety and security, preventing unauthorized users from altering settings of the pump or using the pump in an unauthorized or unsafe manner. Settings managed in the medical infusion pump can include, for example, settings related to pump protocols, pump therapies, qualifiers relating to pump therapies, pump communications settings, user access privileges, security settings, and history data settings. Other settings may be protected and managed using the security systems and access rights protections of the present disclosure.

FIG. 10 illustrates a flowchart of a process 1000 for managing access to features in a medical infusion pump, according to a possible embodiment of the present disclosure. The process 1000 is instantiated at a start operation 1002, which corresponds to initial use of a pump in an infusion pump network.

A user association module 1004 associates a user with the medical infusion pump, providing access to one or more functional aspects of the medical infusion pump for the user. The user association module 1004 establishes the user's ability to log in to the medical infusion pump, and grants that user at least default access rights to view screens relating to the current operational status of the pump.

The user association module 1004 optionally grants additional access rights to one or more systems and settings in a medical infusion pump to the user. The systems and settings in the medical infusion pump can include to settings in a pump and the user's right to view or modify those settings; the systems and settings can also include various modular hardware or software unrelated to protocol selection. In one possible example of settings modifiable in the pump, the user association module 1004 allows the user to view or modify pump protocols or pump parameters, such as the range of acceptable basal delivery rates, drug delivery patterns, bolus delivery times or frequencies, bolus amounts, or other variables related to fluid delivery to a patient. The user can also be allowed to view and modify other pump parameters. In a possible example of accessible systems in the pump, the access rights granted to the user can relate to a bar code scanner, a drug cartridge, a battery compartment, or certain input keys of the pump.

In some embodiments, the user association module 1004 operates at least in part on a computing system communicatively interconnected with a plurality of medical infusion pumps. In such embodiments, the user association module 1004 can associate the user with more than one medical infusion pump, thereby allowing the user to establish a single access rights record used by all pumps. In other embodiments, the user association module 1004 operates in each medical infusion pump, and the user is required to establish a usage rights record in each pump.

The user association module 1004 optionally associates the user with a user class, with the user class having one or more sets of predetermined access privileges. Each user class is configurable to have different access privileges to functionality in a medical infusion pump, and by associating a user with the user class, that user is afforded the access rights given to that class.

In certain embodiments, user classes include an administrative user class, a physician user class, a nurse user class, a pharmacist user class, a patient user class, and other user classes. The administrative user class is granted access to all of the functionality available to the medical infusion pump. The other user classes are granted varying access rights, with the patient class generally provided the least access privileges. For example, while the administrative user class or the physician user class has access to modify pump protocols by modifying one or more of the pump parameters, a patient user class will generally not be given such an access right. The access privileges of the user classes are also optionally modifiable in the medical infusion pump (or a computing system interconnected to the medical infusion pump), such as via user access records and user class association records, for example the records of FIGS. 11-12, below.

A security data association module 1006 associates security data with user who is associated with the medical infusion pump. The security data association module 1006 stores security data that will be used during subsequent use of the medical infusion pump to access functionality by the user. The security data association module 1006 can associate one or more types of security data with each user, allowing the user to gain access to functionality of the medical infusion pump by providing at least one of those types of security data. Security data is data associated with the user that the user can supply to prove his/her identity to the medical infusion pump. In various embodiments, the security data includes a password, an access code, an answer to a security question, an account number, or biometric data, such as a fingerprint pattern, retina scan, or other authorization data.

In certain embodiments, one of which is described in greater detail in part B.3, below, the security data is embodied on an access card useable to gain access to functionality in the medical infusion pump. A user can swipe, scan, or press the access card against a portion of the pump capable of reading the security data (e.g. a magnetic card reader, a touch screen, or an optical scanner) to provide security data to the pump.

In some embodiments, more than one type of security data is accepted. In these embodiments, features of the pump requiring higher security may require multiple types of security data prior to granting access to functionality. For example, a user can be required to enter a password and provide a thumbprint scan to gain access to certain functionality in the medical infusion pump. Other possibilities regarding functionality or combinations of security data are possible as well.

A security data receipt module 1008 receives security data from the user on a subsequent access attempt in the medical infusion pump. The security data receipt module 1008 receives security data of a number of forms, corresponding to the security data associated with the user by the security data association module 1006. The security data receipt module 1008 also compares the received security data to the stored security data associated with the user to determine whether a match exists. If a match between the security data exists, operational flow in the process 1000 proceeds to an access rights determination module 1010. If no match exists, no access rights are afforded to the user.

The access rights determination module 1010 determines the particular functionality accessible to the user, based on the rights established in the user association module 1004. These access rights correspond to the functionality in the medical infusion pump, relating both to mechanical or electrical systems and software settings incorporated into the pump, as previously described. The security data receipt module 1008 and the access rights determination module 1010 can, in certain embodiments, determine access rights based on information in a user access record or user class association record, an example of which is described in conjunction with FIGS. 11-12. In such an embodiment, the user access record 1100 is accessed by the security data receipt module 1008 to determine a match between the one or more types of security data provided by the user and the security data previously associated with the user. Once that match is determined, access rights are established by the access rights determination module 1010, either by reviewing specific access rights granted to the user in the user access record 1100 or by reviewing access rights granted to a user class (of which the user is a part) in the user class association record 1200.

An access module 1012 operates following the access rights determination module 1010 to allow access to a user in accordance with the access rights associated with that user. The access module 1012 only allows access to the various systems and settings in the medical infusion pump that are associated with access rights granted to the user (e.g. through listing in a user access record or a user class association record as in FIGS. 11-12). An optional access denial module 1014 denies access to the user relating to one or more software or hardware/mechanical systems with which that user's usage rights are not associated.

In an example of operation of the access module 1012 and the access denial module 1014, a patient will generally be afforded access rights to certain pump menus and pump settings, allowing the user to administer a bolus or to view operational status of the medical infusion pump with which that patient is associated. The patient can have personalized security data (e.g. an access code or password) or can use a generalized patient login access account. That patient will not be able to access functionality related to certain aspects of the medical infusion pump, such as to edit pump protocols, to use a bar code scanner, or other systems, based on operation of the access denial module. These access rights, however, may be afforded to other users, such as nurses, doctors, or pharmacists. The process 1000 terminates at and end operation 1016, which corresponds to continued operation in accordance with the determined access rights for the user of the pump.

Now referring to FIGS. 11-12, additional details regarding the contents of the user access record 1100 and user class association record 1200 are described, in accordance with an example embodiment of the present disclosure. FIG. 11 illustrates example contents of a user access record 1100 that is used to store and validate security data received from and associated with a user having an account to log in to a medical infusion pump.

The user access record 1100 includes one or more user entries 1102, each of which corresponds to a separate individual having a right to log in to and access information on a medical infusion pump. Each user entry 1102 includes a user name field 1104, one or more security data fields 1106 associated with that user, and one or more access right fields 1108 associated with the user entry 1102. The user name field 1104 corresponds to the name of the individual logging in to the pump, while the security data fields 1106 include the various security data associated with that user, such as an access code, password, bar code, or biometric data.

The access right fields 1108 define the access rights available to a user. The various listed access rights allow different levels or combinations of access rights to settings and systems in the medical infusion pump. In the example shown, various named access rights are listed in the user access record, including an administrative access right, a program access right, a bolus access right, and other access rights. The administrative access right (shown as associated with a user having the name "John Doe") provides full access to view and amend pump protocols, and access to all of the hardware and mechanical features of the medical infusion pump. The program access right allows a user to view the various software features in the medical infusion pump, and to initiate use of a new pump program or protocol in the medical infusion pump. This right may be given, for example, to a nurse who will be required to program the medical infusion pump in accordance with a doctor's order. The program access right may not allow the nurse or other user to alter the parameters included in pump protocols (as would be allowed to a user having an administrative access right), but would allow the user to select a pump protocol for programming the pump. The bolus access level allows a user to administer boluses of the drug or other therapeutic fluid delivered by the pump. This access right can be given, for example, to a patient for management of bolus delivery, without allowing the patient an access right to program the medical infusion pump or alter the pump protocol operating on the medical infusion pump (as would be included in the program access right and the administrative access right).

The user entry 1102 also optionally includes one or more user class fields 1110 which list the user classes to which the user entry (and corresponding user) belongs. The user class fields 1110 provide a reference link within the user access record to a user class association record, such as the record 1200 of FIG. 12. By associating a user with a user class, that user is afforded the access rights of the class with which they are associated.

A user can be associated with more than one access right or class in the user access record 1100. If any of the access rights or classes in the user access record allow the user to perform an action (e.g. altering pump protocols, programming the pump), that user is allowed to perform that action in the medical infusion pump.

FIG. 12 shows an example configuration of a user class association record 1200, which includes one or more user class entries 1202. Each of the user class entries 1202 corresponds to a separate user class associated with one or more access rights. The user classes 1202 listed in the user class association record 1200 allow common combinations of access rights granted to be grouped into a record for ease of use and assignment to users. For example, all doctors will typically be afforded equal access rights to medical infusion pumps. Similarly, patients will all be afforded similar access rights, but those access rights will be different from (more restrictive) than those afforded to doctors. Similar access right distinctions can be made for nurses, pharmacists, or other clinicians.

Each user class entry 1202 is associated with one or more member entries 1204 and one or more access rights entries 1206. The member entries 1204 correspond to users who are members of the class and are designated to receive the access rights of the class; for example, the member entries can correspond to the user entries 1102 of the user access record 1100. The access rights entries 1206 define the access rights associated with the user class entry 1202, and by reference each user identified in the member entries 1204.

Referring now to FIGS. 11-12 generally, in one embodiment, the user access record 1100 and user class association record 1200 can be stored on and managed by a medical infusion pump. In a further embodiment, the user access record 1100 and user class association record 1200 are stored on a computing system communicatively interconnected to one or more medical infusion pumps, as is described in conjunction with the networks of FIGS. 1-2 and 6-7, above.

The access rights afforded to users of the medical infusion pump are optionally definable by editing the records 1100, 1200 using the medical infusion pump or a computing system on which the records reside. The records 1100, 1200 are generally editable by users having administrative access to the pump; certain user entries may also be editable by the user identified by that entry.

The user access record 1100 and user class association record 1200 are depicted as text files that can be stored in a memory of the medical infusion pump or a computing device. However, these records can be configured in a number of alternative formats to that depicted in FIGS. 11-12. In one alternative embodiment, one or both records are stored in a relational database, and can be interrelated to other user records, stored security data (e.g. fingerprint profile files), or other information relevant to access of systems and settings in a medical infusion pump. In a further embodiment, the records are stored as a text file or spreadsheet file, and maintained within a single record file. Other storage configurations are possible as well.

3. Touch Screen User Authentication

Figure 13:
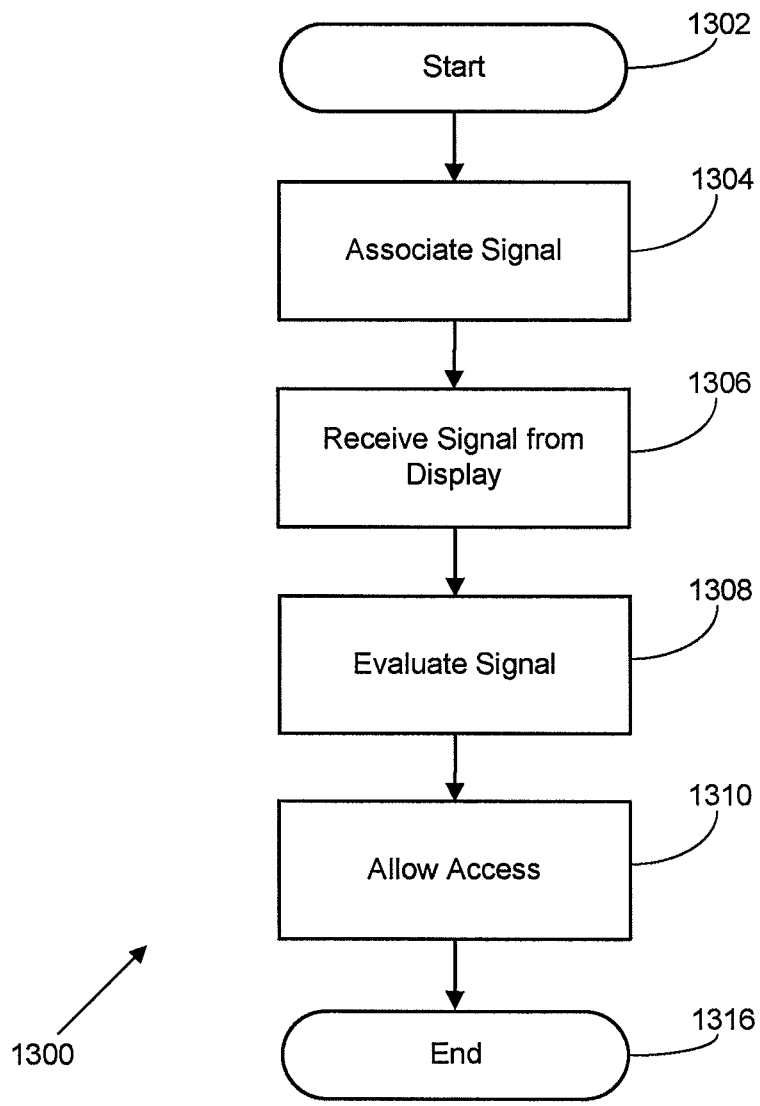
FIG. 13 illustrates a flowchart of methods and systems for authenticating a user in a medical infusion pump, according to a possible embodiment of the present disclosure.
Figure 14:
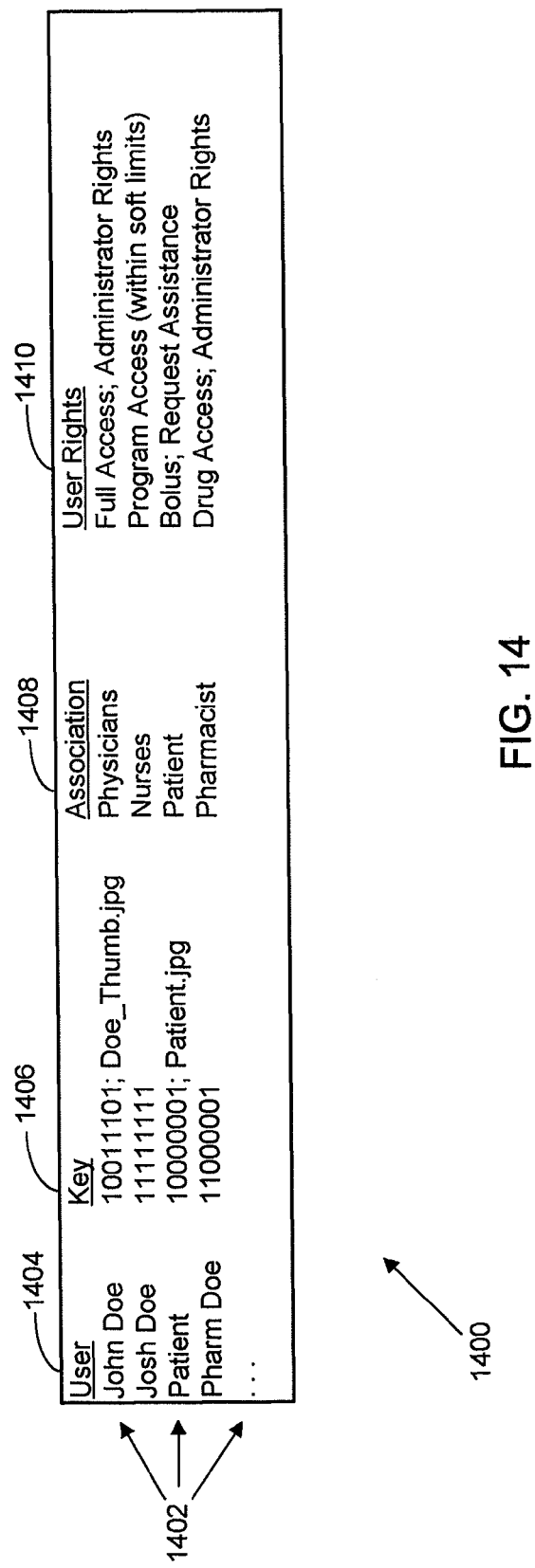
FIG. 14 illustrates a touch screen user authentication record useable in a medical infusion pump, according to a possible embodiment of the present disclosure.
Figure 15:
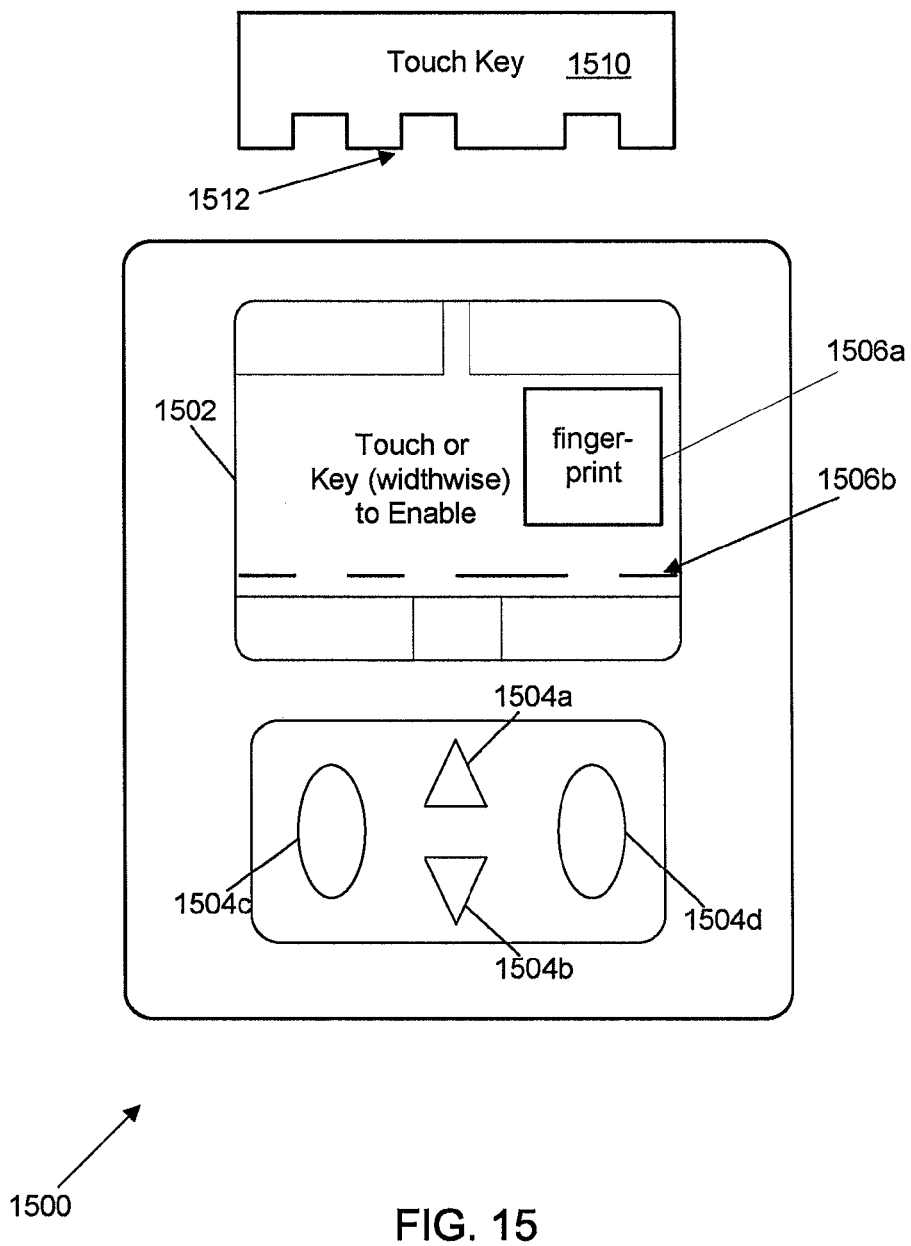
FIG. 15 illustrates a medical infusion pump having a touch screen useable for user authentication, according to a possible embodiment of the present disclosure.

Referring now to FIGS. 13-15, a system for user authentication is described, using a touch screen display integrated into the medical infusion pump. The touch screen display in the medical infusion pump can be, for example, any display described above in conjunction with the display 406 of FIG. 4. The systems described herein can be used in conjunction with the security features of part B.2, above, to authenticate a user in conjunction with security data relating to an input signal received from the touch screen display.

FIG. 13 illustrates a flowchart of a process 1300 for authenticating a user in a medical infusion pump using a touch screen display. The process generally allows a user to touch a display of a medical infusion pump with a hand, keyed card, or other object to validate the identity of the user and allow the user access to various features in the medical infusion pump. The process 1300 is instantiated at a start operation 1302.

A signal association module 1304 associates a signal with a user or user class, and stores a representation of that signal for comparison and authentication of signals received from a user seeking access to features of the medical infusion pump. The signal is generally an analog or digital electrical signal received from a touch screen display of a medical infusion pump. The signal can, in various embodiments, corresponds to a pattern or sequence of touches or motions by a user, or by an object carried by the user. In one example embodiment, the signal corresponds to a digital or analog signal received from a touch-sensitive display based on contact with a keyed, shaped access card, as shown in FIG. 15, below. In a further example embodiment, the signal corresponds to a signal generated in response to a biometric scan, such as a scan or capture of an image of the user, a fingerprint of the user, or other biometric scan information.

The user or user class can be any user or class registrable in the medical infusion pump, such as those described above in FIGS. 10-12. Example users or classes of users include doctors, nurses, patients, pharmacists, technicians, or and clinicians who use, program, repair, or otherwise interact with the medical infusion pump.

In a possible embodiment, the signal association module 1300 associates a generalized signal, such as a known touch action on a touch screen display, with a generalized or default access account on the medical infusion pump (e.g. a default account created in user records as described above in FIGS. 10-12). In such an embodiment, a user touching the display will cause the display to generate the generalized signal and receive access to the medical infusion pump in accordance with the access rights assigned to that generalized or default access account.

A signal receipt module 1306 corresponds to receiving a signal in the medical infusion pump from a display. In some embodiments of the present disclosure, the signal receipt module 1306 receives a signal from a touch screen display, such as a multi-touch display or other type of display described in conjunction with FIG. 4. The signal receipt module 1306 generally receives an analog signal from the display (e.g. based on contact with a touch screen display) and optionally converts that analog signal to a digital signal for comparison with a stored value associated with the user by the signal association module 1304.

A signal evaluation module 1308 compares the signal received by the signal receipt module 1306 with a stored signal associated with a user or a generalized access account to authenticate the user. The signal evaluation module 1308 verifies the identity of the user based on the signal. For example, the signal evaluation module 1308 can compare digital values generated based on a signal with a stored digital value based on a prior signal, as discussed in conjunction with FIGS. 14-15. If the user is recognized by the signal evaluation module 1308, access rights are granted to that user in accordance with the access rights and user record associated with the signal. In certain embodiments, if the user is not recognized by the signal evaluation module 1308, access is denied to the user.

An access module 1310 grants access to a user in accordance with one or more access rights associated with a user record. Examples of access rights and user records are described above in conjunction with FIGS. 10-12. The process 1300 terminates at an end operation 1312, which corresponds to generalized operation of the medical infusion pump by the user, in accordance with the authorized access rights afforded to that user.

FIG. 14 illustrates a touch screen user authentication record 1400 useable in a medical infusion pump, according to a possible embodiment of the present disclosure. The touch screen user authentication record 1400 generally corresponds to the user access record of FIG. 11, but includes information relating to touch screen user authentication systems useable in the medical infusion pump. The touch screen user authentication record 1400 includes a plurality of user records 1402, each of which includes a user field 1404, one or more key fields 1406, and optionally one or more association fields 1408 or one or more user rights fields 1410. Each user record 1402 corresponds to access methods associated with a user, for use in a medical infusion pump having a touch screen authentication system.

The user field 1404 corresponds to the name of the user, and can be used as the name of the user record as well. The key fields 1406 correspond to the signals receivable by the system that would be recognized as a user attempting to use the medical infusion pump. In the embodiment shown, the signals are illustrated as being stored as two types: digitized codes and images of biometric scans. Other types of signals, such as analog signals, could be captured as well by storing certain signature characteristics of those signals. In a possible embodiment of a medical infusion pump using a keyed access card pressed against the touch screen for user validation (e.g. the system of FIG. 15), the digitized codes in the key fields 1406 correspond to the key ridge codes of the access card. An example of an access card and corresponding touch screen digitized code is shown in FIG. 15.

The association fields 1408 generally correspond to the user class fields described above in conjunction with FIGS. 10-11, but can also include common authentication data used by groups of users. In certain embodiments, the association fields refer to groups of users sharing at least one common key field. Using that common key field, users in the user class can access settings and systems in the medical infusion pump according to the common access rights of that user class.

The user rights fields 1410 correspond generally to the access rights described in the records of FIGS. 10-11, and define access rights for one or more users associated with information in the key fields of the same user record 1402. Alternatively to including the user rights fields 1410 in the touch screen user authentication record 1400, the system can link to user rights in a user access record or user class association record, such as are described above in conjunction with FIGS. 10-11.

The user authentication record 1400 as described herein is intended as an example embodiment of a data structure in which access rights and security data can be managed. As with the records 1000, 1100, the touch screen user authentication record 1400 can include various other information, or can be embodied in a variety of other formats of databases or other data structures.

FIG. 15 illustrates a medical infusion pump 1500 having a touch screen operable for user authentication, according to a possible embodiment of the present disclosure. The medical infusion pump 1500 generally corresponds to the medical infusion pumps described in FIGS. 1 and 4-5, and includes a touch screen user interface 1502, and soft keys 1504a-d. The touch screen user interface 1502 is any of a variety of types of touch-sensitive interfaces such as those described above in conjunction with the display 406 of FIG. 4.

In the embodiment shown, the touch screen user interface 1502 includes one or more regions 1506a-b configured to accept a touch from a user, access card, or other keyed access method applied to the display, and generate a signal in response to that touch for the purposes of user authentication. Specifically shown are a fingerprint region 1506a and a keyed access contact region 1506b; however, other regions can be included as well. The fingerprint region 1506a acts as a fingerprint reader for the medical infusion pump, and can be integrated into the display 1502 or a separate display region. The fingerprint region 1506a receives a fingerprint and generates an analog signal or captures an image of the fingerprint (based, for example, on pressure or imaging) for authentication using a key in a touch screen user authentication record, such as the record 1400 of FIG. 14. The keyed access contact region 1506b accepts contact with a keyed access card 1510, which includes a keyed pattern 1512 on at least one edge of the card. The keyed pattern 1512 corresponds to a digital code stored in an authentication record (e.g. the record 1400 of FIG. 14) to authenticate a user who is a holder of the keyed access card 1510. When the keyed pattern 1512 is depressed against the keyed access contact region 1506b, a signal is generated by the display representative of a code identifying the user, thereby authenticating that user's access to the systems and settings of the medical infusion pump.

The soft keys 1504a-d provide an alternative method of controlling the pump, allowing a user to key in an access code or other options (e.g. confirming the touch access) during the authentication process, as required.

The above specification, examples and data provide a complete description of the manufacture and use of the composition of the invention. Since many embodiments of the invention can be made without departing from the spirit and scope of the invention, the invention resides in the claims hereinafter appended.

The invention claimed is:

1. A system for selectively granting a patient limited rights to alter delivery of a medicament from a medical infusion pump to the patient within a range specific to the patient, thereby providing enhanced safety and security to the patient, the system comprising:
- an administrator computer communicatively coupled with the medical infusion pump enabling an administrator to define:
  - at least one pump protocol for the medical infusion pump defining a patient-specific range of values and patterns for delivery of a medicament, and
  - a user access record for the medical infusion pump associating the patient with a security signal and at least a patient user class, wherein the patient user class is assigned one or more limited access rights to the medical infusion pump;
- a medical infusion pump having a programmable circuit communicatively coupled to a memory previously loaded with an application program, the programmable circuit regulating delivery of the medicament to the patient in accordance with at least one pump protocol defining a patient-specific range of values and patterns for delivery of a medicament, the at least one pump protocol executed in the context of the application program, the medical infusion pump further having a user input device; and
- a server communicatively connecting the administrator computer to the medical infusion pump, wherein the at least one pump protocol and the one or more limited access rights are communicated to the medical infusion pump, the one or more limited access rights assigned to the patient user class enabling the patient to alter delivery of the medicament within the at least one pump protocol defined patient-specific range of values and patterns for delivery of the medicament if a security signal received by the user input device matches the user access record security signal.

2. The system of claim 1, further comprising associating the patient with at least one additional user class, wherein each user class is assigned one or more access rights.

3. The system of claim 2, wherein the at least one additional user class is a class selected from the group consisting of:
- nurses;
- physicians;
- clinicians;
- pharmacists;
- technicians; and
- users having administrative access to the medical infusion pump.

4. The system of claim 1, wherein the one or more limited access rights include the ability to alter at least one of:
- a range of permissible basal delivery rates;
- a bolus amount;
- a fluid delivery amount; and
- a range of values and patterns for extended boluses.

5. The system of claim 1, wherein the security signal is at least one of:
- a password;
- a security code;
- a bar code; and
- a biometric identifier.

6. A method for selectively granting a patient a limited right to alter delivery of a medicament from a medical infusion pump to the patient within a range specific to the patient, thereby providing enhanced safety and security to the patient, the method comprising:
- generating a pump protocol for the medical infusion pump with an infusion pump network, the pump protocol defining a patient-specific range of values and patterns for delivery of a medicament;
- generating a user access record for the medical infusion pump with the infusion pump network, the user access record associating the patient with a security signal and a patient user class, wherein the patient user class is assigned one or more limited access rights to the medical infusion pump;
- operating a programmable circuit of the medical infusion pump in accordance with at least one pump protocol defining a patient-specific range of values and patterns for delivery of a medicament, the at least one pump protocol executed in the context of an application program previously loaded into the memory of a medical infusion pump to regulate delivery of medicament to the patient;
- receiving a security signal at a user input device of the medical infusion pump;
- evaluating the security signal to determine if the received security signal matches the user access record security signal; and
- enabling the patient to alter delivery of the medicament within the pump protocol defined patient-specific range of values and patterns for delivery of the medicament according to the one or more limited access rights assigned to the patient user class if the received security signal matches the user access record security signal.

7. The method of claim 6, wherein the security signal is at least one of:
- a password;
- a security code;
- a bar code; and
- a biometric identifier.

8. The method of claim 6, further comprising associating the security signal with the patient.

9. The method of claim 6, further comprising denying the user the ability to alter delivery of the medicament if the received security signal does not match the user access record security signal.

10. The method of claim 6, wherein the one or more limited access rights include the ability to alter at least one of:
- a range of permissible basal delivery rates;
- a bolus amount;
- a fluid delivery amount; and
- a range of values and patterns for extended boluses.

11. The method of claim 6, further comprising associating the patient with at least one additional user class, wherein each user class is assigned one or more access rights.

12. The method of claim 11, wherein the at least one additional user class is a class selected from the group consisting of:
- nurses;
- physicians;
- clinicians;
- pharmacists;
- technicians; and
- users having administrative access to the medical infusion pump.

13. A system for selectively granting a patient a limited right to alter delivery of a medicament from a medical infusion pump to the patient within a range specific to the patient, thereby providing enhanced safety and security to the patient, the system comprising:
- an administrator computer communicatively coupled with the medical infusion pump and configured to generate a pump protocol for the medical infusion pump, the pump protocol defining a patient-specific range of values and patterns for delivery of a medicament;

a database configured to store a user access record for the medical infusion pump, the user access record associating the patient with a security signal and a patient user class, wherein the patient user class is assigned one or more limited access rights to the medical infusion pump;

a user input device communicatively coupled to the medical infusion pump and configured to receive a security signal;

a programmable circuit of the medical infusion pump configured to regulate delivery of medicament to the patient in accordance with at least one pump protocol defining a patient-specific range of values and patterns for delivery of a medicament, the at least one pump protocol executed in the context of an application program previously loaded into the memory of a medical infusion pump, wherein the programmable circuit enables the patient to alter delivery of the medicament within the pump protocol defined patient-specific range of values and patterns for delivery of the medicament according to the one or more limited access rights assigned to the patient user class if the received security signal matches the user access record security signal.

* * * * *